(12) United States Patent
Fiedler et al.

(10) Patent No.: US 11,676,689 B2
(45) Date of Patent: Jun. 13, 2023

(54) INTERACTIVE ELECTRONIC COMMUNICATIONS AND CONTROL SYSTEM

(71) Applicant: ACESO, Charlestown, MA (US)

(72) Inventors: Geoff Fiedler, Falmouth, MA (US); Todd Babineau, Wilbraham, MA (US); Dennis Mathur, Massapequa, NY (US); Tianbin Zhao, Irvine, CA (US)

(73) Assignee: ACESO, Charlestown, MA (US)

( * ) Notice: Subject to any disclaimer, the term of this patent is extended or adjusted under 35 U.S.C. 154(b) by 91 days.

(21) Appl. No.: 17/117,437

(22) Filed: Dec. 10, 2020

(65) Prior Publication Data
US 2021/0104305 A1 Apr. 8, 2021

Related U.S. Application Data

(63) Continuation of application No. 15/810,325, filed on Nov. 13, 2017, now Pat. No. 10,916,336.
(Continued)

(51) Int. Cl.
| | |
|---|---|
| *G16H 10/60* | (2018.01) |
| *G06F 16/23* | (2019.01) |
| *G06F 16/25* | (2019.01) |
| *G16H 40/20* | (2018.01) |
| *G06F 40/205* | (2020.01) |
| *H04W 12/50* | (2021.01) |
| *H04L 67/75* | (2022.01) |

(Continued)

(52) U.S. Cl.
CPC ......... *G16H 10/60* (2018.01); *G06F 16/2379* (2019.01); *G06F 16/25* (2019.01); *G06F 40/205* (2020.01); *G06Q 30/0281* (2013.01); *G16H 40/20* (2018.01); *H04L 67/75* (2022.05); *H04W 12/06* (2013.01); *H04W 12/50* (2021.01); *H04L 63/08* (2013.01); *H04W 12/77* (2021.01); *H04W 84/12* (2013.01)

(58) Field of Classification Search
CPC .... G16H 10/60; G16H 40/20; G06F 16/2379; G06F 16/25; G06F 40/205; G06Q 30/0281; H04L 67/75; H04L 63/08; H04W 12/06; H04W 12/50
See application file for complete search history.

(56) References Cited

U.S. PATENT DOCUMENTS

| | | |
|---|---|---|
| 8,229,759 B2 | 7/2012 | Zhu et al. |
| 9,439,734 B2 | 9/2016 | Beaudry |

(Continued)

OTHER PUBLICATIONS

ACESO, Marketing Brochure, 2011, USA.
ACESO, Marketing Brochure, 2012, USA.

*Primary Examiner* — Huawen A Peng
(74) *Attorney, Agent, or Firm* — Rothwell, Figg, Ernst & Manbeck, P.C.

(57) ABSTRACT

A system comprising a database containing user data, an interface engine that communicates with the database and parses the data, an application server that communicates with the interface engine, a user device that receives and displays the parsed data, receives user-provided information, and sends the user-provided information to the application server, wherein the application server automatically updates the user device display with the parsed data, receives user-provided information from said user device, and provides the user-provided information to the interface engine for updating the database.

14 Claims, 21 Drawing Sheets

Related U.S. Application Data

(60) Provisional application No. 62/551,402, filed on Aug. 29, 2017, provisional application No. 62/420,945, filed on Nov. 11, 2016.

(51) Int. Cl.
   *G06Q 30/02* (2023.01)
   *H04W 12/06* (2021.01)
   *H04L 9/40* (2022.01)
   *H04W 12/77* (2021.01)
   *H04W 84/12* (2009.01)

(56) References Cited

U.S. PATENT DOCUMENTS

| | | | |
|---|---|---|---|
| 9,652,960 B2 | 5/2017 | Flinsenberg et al. | |
| 9,690,538 B1 | 6/2017 | Doyle, III et al. | |
| 9,996,678 B2 | 6/2018 | Johnson | |
| 10,037,821 B2 * | 7/2018 | Johnson | G06Q 10/06395 |
| 2008/0021730 A1 * | 1/2008 | Holla | G16H 10/60 |
| | | | 705/2 |
| 2008/0178258 A1 | 7/2008 | Loomis | |
| 2008/0262867 A1 * | 10/2008 | Bayne | G06Q 10/109 |
| | | | 705/2 |
| 2013/0024382 A1 * | 1/2013 | Dala | H04L 63/0464 |
| | | | 705/51 |
| 2013/0054467 A1 * | 2/2013 | Dala | G06F 21/6245 |
| | | | 705/51 |
| 2013/0074167 A1 | 3/2013 | Bailey et al. | |
| 2013/0262155 A1 * | 10/2013 | Hinkamp | G16H 10/60 |
| | | | 705/4 |
| 2013/0326421 A1 | 12/2013 | Jo | |
| 2015/0012443 A1 | 1/2015 | Bhat et al. | |
| 2015/0324525 A1 | 11/2015 | Saffran | |
| 2016/0259413 A1 | 9/2016 | Anzures et al. | |
| 2016/0302210 A1 * | 10/2016 | Thornton | G01S 5/14 |
| 2016/0328577 A1 | 11/2016 | Howley | |
| 2017/0169170 A1 * | 6/2017 | Otin | H04W 4/80 |

* cited by examiner

| Mon. March 7 2016 | Jonathon Smith<br>Oncology – Room 2105<br>Phone: (413) 279-2105 | 12:30<br>PM |

↑↓ My Medications ~590
Last PRN: Vicodin / Date/Time: 2016-03-07 08:30 AM

Atorvastatin (Lipitor®) – Cholesterol lowering drug ~596
Used to reduce the risk of heart attack and stroke by decreasing cholesterol build-up on the walls of arteries Common Side Effects:
- Diarrhea
- Heartburn
- Joint pain
- Forgetfulness Contact a nurse if you have:
- Muscle pain or weakness
- Fever or nausea
- Chest pain
- Extreme tiredness

Captopril (Capoten) – ACE Inhibitor ~596
In combination with other medications, treats high blood pressure and heart failure.

Common Side Effects:
- Dizziness or lightheadedness
- Salty or metallic taste
- Cough Contact a nurse if you have:
- Chest pain
- Swelling of the face, eyes, lips, tongue, arms, or legs
- Hives

Furosemide (Lasix) – Diuretic ~596
Used to treat edema (fluid retention; excess fluid held in body tissues) caused by heart, kidney, and liver disease.

Common Side Effects:
- Frequent urination
- Blurred vision

Contact a nurse if you have:
- Fever
- Hearing loss or "ringing"
- Rash or hives
- Blisters or peeling skin

Metoprolol (Lopressor) – Beta Blocker ~596
Treats high blood pressure, chest pain and heart failure.

Common Side Effects:
- Dizziness
- Tiredness

Contact a nurse if you have:
- Fainting
- Swelling in hands, feet
- Trouble breathing

| My Care | My Meds | My Medical Notes | Sleep |

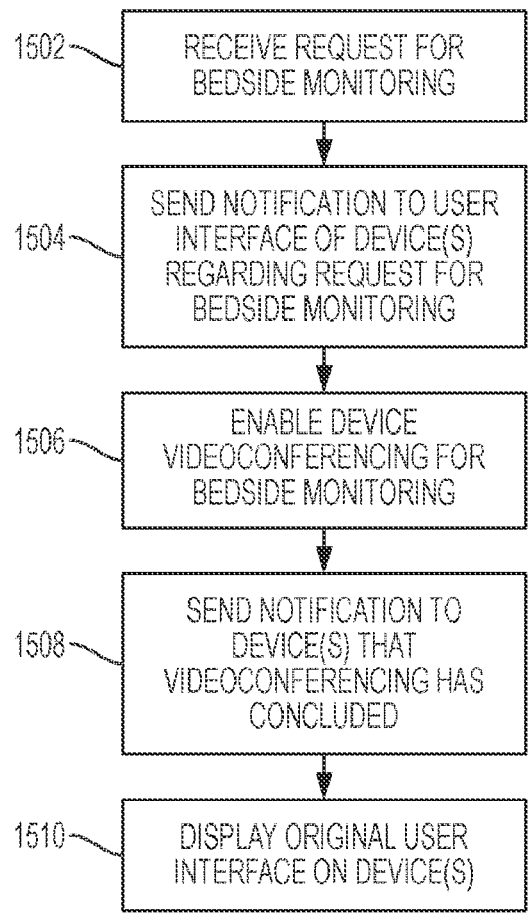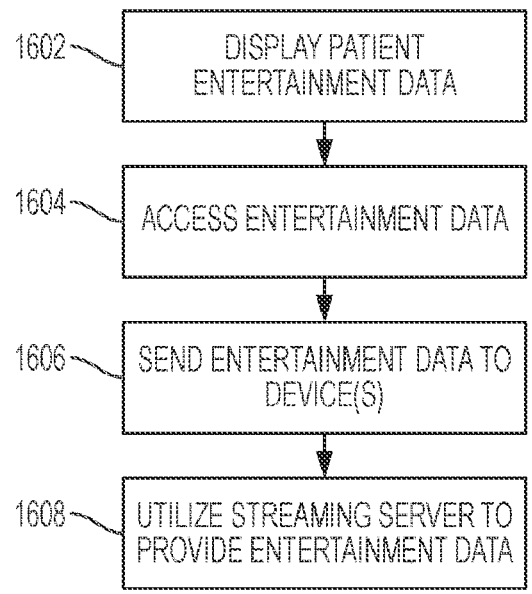
FIG. 15
FIG. 16

INTERACTIVE ELECTRONIC COMMUNICATIONS AND CONTROL SYSTEM

CROSS-REFERENCE TO RELATED APPLICATIONS

This application is a continuation of U.S. application Ser. No. 15/810,325, filed Nov. 13, 2017, which claims the benefit of and priority to U.S. Provisional Application Nos. 62/420,945, filed Nov. 11, 2016 and 62/551,402 filed Aug. 29, 2017, which are each incorporated herein by reference in their entirety for all purposes under the law.

FIELD OF THE INVENTION

The subject matter disclosed herein generally relates to an interactive electronic communications and control system tailored for facilities in any number of industries. The disclosure focuses on the healthcare industry, describing systems, devices and methods for the communication, control and interactive sharing of, for example, admission, medical, educational, diet, entertainment and other parsed data and content relating to a patient's medical condition, treatment and stay at a healthcare institution. It will be understood that the invention is not limited to applications in the healthcare industry but can also be applied to other industries as well including industries where tailored content is provided to specialized audiences, allowing for high-level interaction between those audiences and the system to advance institutional and other objectives.

BACKGROUND OF THE INVENTION

As of 2016, there were over 5,000 registered hospitals, nearly 900,000 staffed beds, and over 35,000,000 patient admissions in the United States alone. (Source: American Hospital Association 2017 Fast Facts that can be found at http://www.aha.org/research/re/stat-studies/fast-facts.shtml).

Healthcare institutions (e.g., hospitals, multiple facility healthcare systems, and other single or multiple facility healthcare institutions) have historically focused on improving the quality of care, efficiency of care, and quality of stay for their patients. Patient-related data, such as patient medications, lab results, physician assignments, room assignments, and other key information have been used in one way or the other to attempt to help satisfy these objectives.

Over the years, serious challenges arose, and still exist today, relating to the utilization of such information. For example, patient information, especially in today's high-tech healthcare environment, can be very complex, and major compatibility issues often exist between the variety of hardware and software systems that institutions utilize in storing and managing such information.

Furthermore, as institutions utilize more information from outside of the institutions themselves, a greater amount of resources have gone into devising systems that seek to access information from a significant number of external disparate sources. Systems configured to attempt to address these complex issues have required numerous customized components (e.g., local and remote physical servers) organized in a complex manners giving rise to significant installment and maintenance costs, inefficiencies and technical problems.

As described herein, the present invention resolves these and other problems by providing systems, devices and methods generally locally at the institution site utilizing virtual machine servers combined with appropriate novel integration and application programs. This approach, as described herein, enhances the delivery of information within a healthcare institution in many respects, including allowing the system to operate within many diverse host environments and datacenters to provide, for example, enhanced disaster recovery, uptime and scalability.

This approach also eliminates the need to rely on third party video streaming vendors, the need to supply hardware on site, and provides a specialized information system unique to the healthcare industry, eliminating the need to adapt applications built to serve datacenter infrastructure of other industries, such as the hotel industry. This approach is also beneficial because the system does not have to rely upon and draw from disparate hardware and software sources and third party proprietary equipment to function in the manner as described herein.

In other aspects, institutions and other organizations utilize localized media and communications systems to communicate and interact with specific audiences by, among other things, providing specialized media content and services to those audiences. For example, healthcare institutions utilize such systems to present specialized media content to inpatients relating to their care, and to allow patients to each give and receive tailored healthcare information about their respective health conditions and stays. Other such media and communication systems operate within other institutions such as hotels, businesses, schools, homes, and other facilities and locations.

Among the persistent problems in operating such local media and communications systems are the limitations of the user remote control device in operating end user devices such as television sets. For example, in a hospital setting, a user will often utilize a "pillow speaker" remote control device, typically hardwired into each system. Other remote controls, utilizing infrared signal technology, are also utilized.

Significant limitations exist with the control functionality of pillow speaker and other remote control devices. For example, patients have varying needs and gross motor and fine motor abilities, and manipulating the often large and clumsy pillow speakers and other remote control devices can be challenging. Furthermore, with respect to pillow speakers, such devices often introduce a lag time and the control buttons can be difficult to press. Pillow speakers and other remote control devices also have a limited number of buttons, limiting the amount of controls the user can utilize to control the endpoint device.

Other problems include certification of new TV models, which change at a very frequent pace, certification and corresponding firmware changes to Television Control Modules and Set Back Boxes to allow control of new TV models, the fact that different codes-sets on pillow speakers work with different TV manufacturers/models, limitations in the number of buttons/codes or available functionality based on Pillow Speaker manufacturer agreements with Nurse Call systems, the typically lengthy process for creation of new pillow speakers and/or overlays, lack of ease of navigation within control menus for certain patient populations, due to the construction of the devices in accordance with healthcare standards which require that the devices be cleaned frequently.

Other remote controls, for example remote controls utilizing infrared signals, suffer from similar problems in that different remote controls work with different TV models/manufacturers, having only a limited number of user buttons, lack of ease in navigating through menu screens since there needs to be direct line-of-sight between the remote and the TV, and need to meet healthcare standards in their ability to be cleaned.

The present invention solves these problems with a significant advancement in local system control technology. Specifically, as shown and described herein, the present invention utilizes a mobile application and wireless local area networking systems to control navigation at the application server level, allowing for an advanced ability to navigate, manage content, and communicate within a given media and communications system. Overall, the present invention is therefore a significant advancement in the field institution computer technology allowing users to achieve key outcomes.

SUMMARY OF THE INVENTION

In accordance with one embodiment of the invention, a system is provided wherein the system comprises a database, wherein said database contains user data; an interface engine, wherein said interface engine is configured to communicate with said database and parse said user data; an application server, wherein said application server is configured to communicate with said interface engine; a user device, wherein said user device is configured to receive and display said parsed data, receive user-provided information, and send said user-provided information to said application server; and wherein said application server is configured to automatically update a display of said user device with one or more aspects of said parsed data, receive user-provided information from said user device, and provide said user-provided information to said interface engine for updating said database.

In another exemplary embodiment of the invention, a method is provided comprising receiving user data from a database, parsing said user data to create parsed data; storing said parsed data; sending admission data to an application server; confirming that said admission data corresponds to an available user device; sending said parsed data to said device so that said device can display said parsed data; automatically updating said parsed data to create updated parsed data; and automatically displaying said updated parsed data on said display of said device.

In another exemplary embodiment of the invention, a system is provided comprising an application server, a wireless local area network, a user device, an endpoint device, wherein said user device is configured to send one or more commands to said application server over said local area network, said endpoint device is configured to receive and execute said commands as instructed from said applications server, and said endpoint device is configured to display media content on a display of said endpoint device corresponding to said commands.

In another exemplary embodiment of the invention, a method is provided comprising communicating with a facility application program over a wireless local area network, wherein such communication is performed by a user application program operating on a user device; authenticating user information of a user of said user device, wherein said authentication is performed by said facility application program; pairing said user device with an endpoint device, wherein said endpoint device is configured to display media content; displaying one or more control icons on said user device, wherein said one or more control icons are configured to receive command instructions from said user of said user device; sending one or more commands to said facility application program through haptic contact engagement with said one or more control icons; and controlling said endpoint device to display said media content corresponding to said one or more commands.

The above and other various aspects and embodiments are described below with reference to the accompanying drawings.

BRIEF DESCRIPTION OF THE DRAWINGS

The accompanying drawings, which are incorporated herein and form pan of the disclosure, help illustrate various embodiments of the present invention and, together with the description, further serve to describe the invention to enable a person skilled in the pertinent art to make and use the embodiments disclosed herein.

In the drawings, like reference numbers indicate identical or functionally similar elements.

FIG. 5H illustrates another aspect of a user interface utilized by an interactive communications and control system within a healthcare institution, as shown and described herein.

FIG. 15 illustrates another aspect of a method for the interactive sharing of information within a healthcare institution, as shown and described herein.

FIG. 16 illustrates another aspect of a method for the interactive sharing of information within a healthcare institution, as shown and described herein.

DETAILED DESCRIPTION OF THE INVENTION

Figure 1:
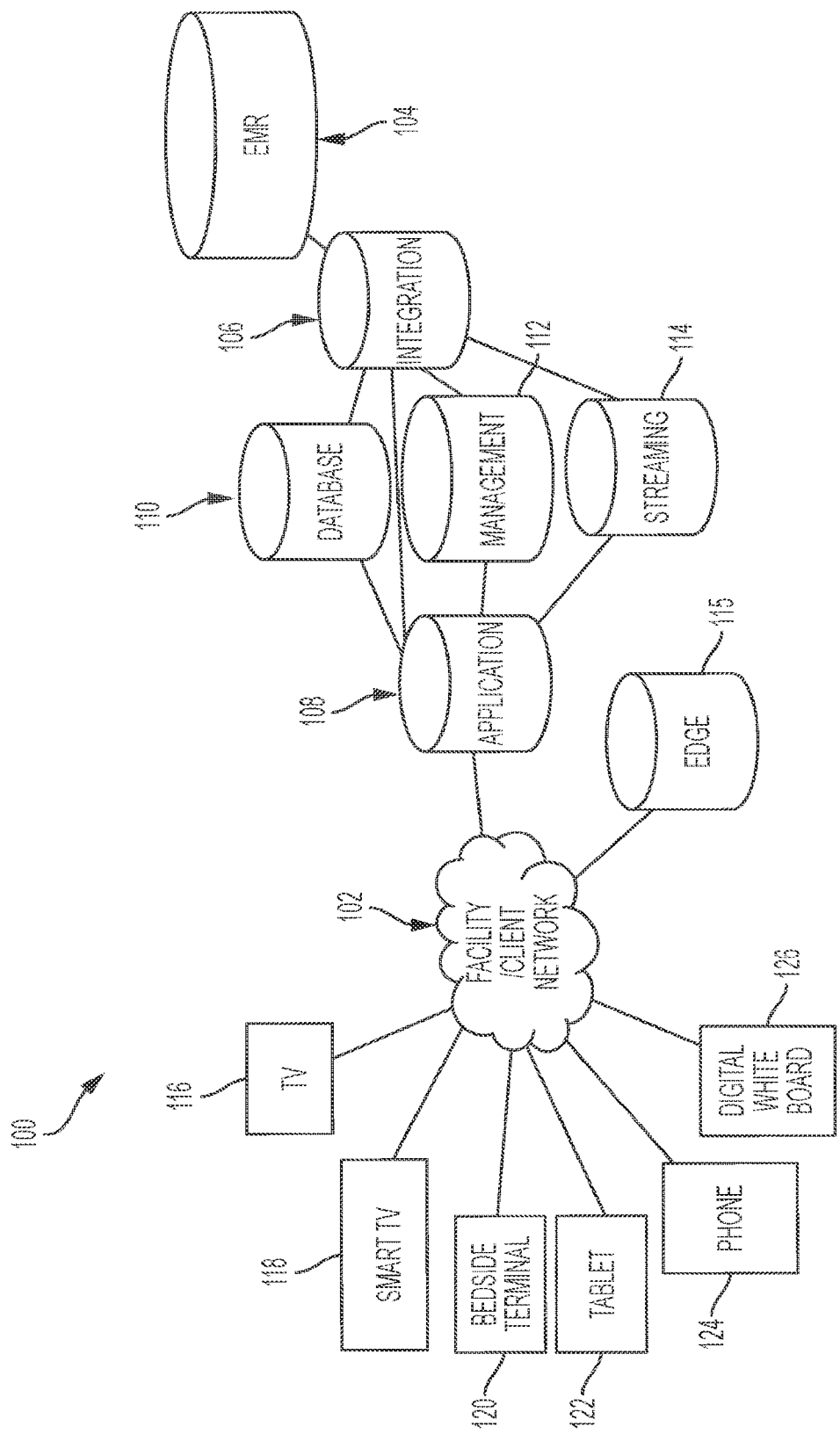
FIG. 1 illustrates an interactive communications and control system within a healthcare institution as shown and described herein.

Referring now to FIG. 1, an embodiment of an electronic communications system 100 for the interactive sharing of information within a healthcare institution is shown.

The system 100 includes a number of hardware and software components designed to communicate across a local area network 102, wide area network, or other functional network to allow for the interactive sharing of information relating to a patient's care and stay at a healthcare institution.

In this embodiment, as will be described in more detail below, the components of the system 100 include an integration server 106, an application server 108, a database server 110, a management server 112, a streaming server 114, and one or more types of user devices including, but not limited to, a standard television 116, a smart television 118, a bedside terminal 120, a smart tablet 122, a smart phone 124, and a digital white board terminal 126.

These and other system 100 hardware and software components are configured to communicate with an electronic medical records (EMR) system 104, typically belonging to or otherwise operated by the healthcare or other institution where the system 100 is implemented. It will be understood that any number of other like components can be added to the system 100 to accomplish the objectives of the system 100 as described herein. It will also be understood that an edge server 115 can also be utilized when one or more of the other system 100 servers and other components are located off site. The edge server 115 is configured to allow communication between such offsite system 100 components and onsite system 100 components in order to allow proper functioning of the system 100 as described herein.

Figure 2:
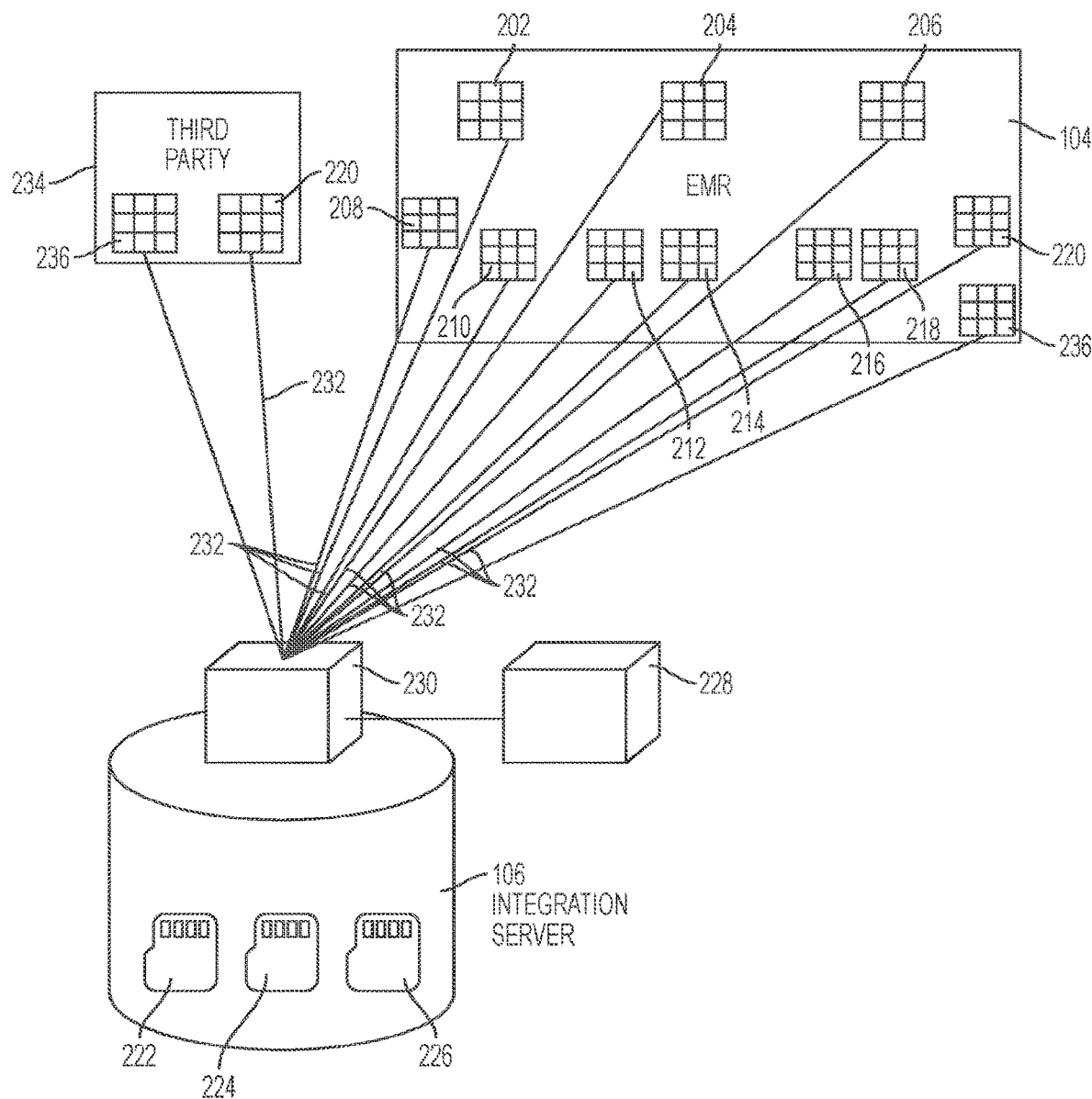
FIG. 2 illustrates another aspect of an interactive communications and control system within a healthcare institution, as shown and described herein.

Referring now to FIG. 2, another aspect of the system 100 is shown. Here, each healthcare institution will have one or more EMR systems 104 that are institution-based full applications that store, have access to, and manage multiple data sets relating to each patient based on the workflows in a given healthcare institution or healthcare system. It will be understood that the EMR system 104 could utilize local servers, third party servers, or other components or databases configured to store, distribute and otherwise manage such data. It will be further understood that the EMR system 104 can reside on a single server or location, or reside on multiple servers or locations located within or outside of the facility in the vicinity of the system 100 or not.

The EMR system 104 contains information relating to a number of categories of patient and health information. This information is exchanged with system 100 through a variety of messages and transaction types relating to, among other things, patient ADT data (admissions, discharge, transfer and other patient-related data) 202, patient medication data 204, nursing assessment data 206, orders and results data 208, diet orders data 210, and patient education data 212 data.

In addition, the system 100 enhances the patient experience by providing patients with the ability to submit requests and feedback data 214, submit meal orders data 216, and submit HVAC control data (e.g., temperature control) 218 to the system 100 through user interfaces of each patient's device (e.g., smart television 118). This data, and other feedback data (e.g., relating to patient education feedback data 212) is channeled through the application server 108 and/or integration server 106, and exchanged with the EMR system 104, third party vendor applications, or other applications as appropriate.

The system 100 also enhances data received from the EMR system 104 when that data 220 might not be meaningful to a patient in the format in which it is stored on the EMR system 104. For example, patient diet orders data 210 received from the EMR system 104 as "NPO2" might be mapped in the EMR system 104 as: "Nil per os." "Nil per os" is a Latin phrase meaning "nothing by mouth" restricting all oral food and fluids, and the system 100 is configured to present that data in plain English, or other languages, to the patient on one or more system devices.

Similarly, drug information 204 received from the EMR system 104 might have a variety of codes that the system 100 translates into plain language. For example, the EMR system 104 might provide a code: 23490647801, which the system will translate into "Warfarin" (the national NDC code for Warfarin is 23490647801). The system 100 is configured to query such information from third party vendors to obtain and display information in a patient-friendly format like "What is the drug used for", "What are some adverse effects," and display the corresponding information in plain language on one or more of the patient devices.

It will be understood that the above categories of information are provided as examples, and other categories of information could also be the subject of the operation of the system 100, devices and methods as described herein.

The system 100 also includes an integration server 106. In this embodiment, the integration server 106 is a virtual machine server configured to utilize one or more storage memory components 222 and utilize, interact with, or otherwise reside within the infrastructure of each given healthcare institution.

The storage memory components 222 can include one or more computer readable storage mediums 224 designed to store executable instructions such as computer code, and one or more other storage memory components 226 designed to store other data utilized during the operation of the system 100.

The integration server 106 is configured with a third party interface engine 230 that allows, in conjunction with an integration application program 228, for the receiving, sending and separation of a variety of messages and message types to and from the EMR system 104 and other system 100 servers and components using a variety of standards and protocols.

The integration application program 228 is also stored on the integration server 106 on one or more of its storage memory components 222, such as a computer readable storage medium 224, and is configured to communicate with the interface engine 230 to allow for the receiving, sending and separation of a variety of messages and message types to and from the EMR system 104 and other system 100 servers and components pursuant to the operation of the system 100 as described herein.

In the present embodiment, the interface engine 230 contains channels or pipes 232, which communicate with the EMR system 104, and contain operational instructions to access, parse and update information transacted with the EMR system 104 and other third party systems 234. Such information includes, but is not limited to, the ADT data (admissions, discharge and transfer) 202, medications data 204, nursing assessment data 206, orders and results data 208, diet orders data 210, education data 212, patient requests and feedback data 214, patient meal order 216 data, HVAC control data 218, patient friendly medication data 220, and other data 236.

The integration application program 228 is configured to communicate with the interface engine 230 and create and store parsed data sets corresponding to the accessed data, sets, including parsed ADT data (admissions, discharge and transfer) 202, medications data 204, nursing assessment data 206, orders and results data 208, diet orders data 210, education data 212, patient requests and feedback data 214, meal ordering data 216, HVAC data 218, patient friendly medication data 220, and other corresponding data 236.

It will be further understood that the integration application program 228 operating on the integration server 106 is configured to act upon the parsed data identified above in a number of different ways depending upon the type and complexity of the messages and data in each data set. In some cases, the parsed data will be stored (on any of the storage memory components of the system 100). In other cases, the parsed data will be sent to the application server 108 for utilization in the system 100.

It will be further understood that the integration application program 228 operating on the integration server 106 is configured to receive data from the various system components (e.g., the application server 108) and in some circumstances communicate data, including updated information, to the EMR system 104.

The integration server 106 and integration application program 228 are also configured to communicate with the other servers, programs, and components of the system 100 across the network 102 in accordance with the operation of the system 100 as described herein.

Figure 3:
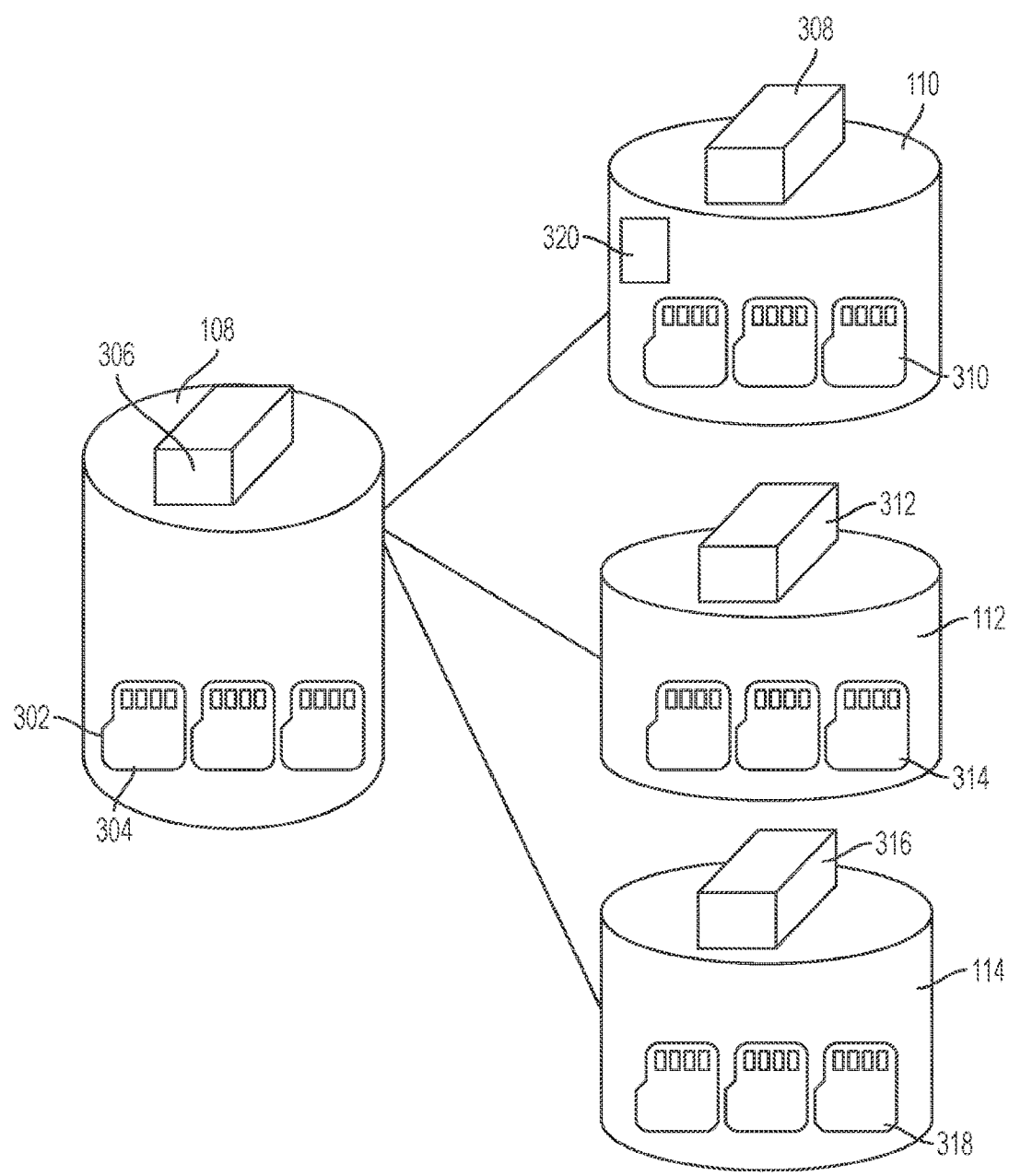
FIG. 3 illustrates another aspect of an interactive communications and control system within a healthcare institution, as shown and described herein.

Referring now to FIG. 3 another aspect of the system 100 is shown. Here, the system 100 also includes an application server 108. In this embodiment, the application server 108 is a virtual machine server configured to utilize one or more storage memory components 302 and utilize, interact with, or otherwise reside within the infrastructure of each given healthcare institution.

The storage memory components 302 can include one or more computer readable storage mediums 304 designed to store executable instructions such as computer code, and one or more other storage memory components 302 designed to store other data utilized during the operation of the system 100.

The application server 108 is configured to store a system application program 306 on one or more of its storage memory components 302, such as a computer readable storage medium 304. The system application program 306 contains operational instructions to manage the operation of the system 100, including, but not limited to, sending, receiving and managing information amongst the various components of the system 100 to ensure proper operation of the system 100.

The system application program 306 is also configured to call, communicate with, or otherwise rely upon several other servers and programs within the system 100. For example, the system application program 306 is configured to call, communicate with, or otherwise rely upon integration server application program 228 residing on the integration server 106. This communication is important for, among other things, the sending, receiving and updating of data transacted with the facility EMR system 104, user interfaces and other components of the system 100.

The system application program 306 is also configured to call, communicate with, or otherwise rely upon a database server 110. In this embodiment, the database server 110 is a virtual machine server configured to store various system and patient data 320 including text and media (e.g., video) content, as well as certain operational computer code 308, on one or more storage memory components 310. The database server 110 is also configured to utilize, interact with, or otherwise reside within the infrastructure of each given healthcare institution.

The system application program 306 is also configured to call, communicate with, or otherwise rely upon a management server 112. In this embodiment, the management server 112 is a virtual machine server configured to store various system tools 315, as well as certain operational computer code 312, on one or more storage memory components 314. The management server 112 is also configured to utilize, interact with, or otherwise reside within the infrastructure of each given healthcare institution.

The system application program 306 is also configured to call, communicate with, or otherwise rely upon a streaming server 114. In this embodiment, the streaming server 114 is a virtual machine server configured to store video and other media content, tools to assist with the streaming of video content, as well as certain operational computer code 316, on one or more storage memory components 318. The streaming server 114 is also configured to utilize, interact with, or otherwise reside within the infrastructure of each given healthcare institution.

It will be further understood that the application program 306 operating on the application server 108 is configured to act upon the data it accesses and receives in accordance with the desired functioning of the system 100. In some cases the data will be stored, in other cases logical operations will be performed on the data, and in other cases the data will be relayed to other system 100 components for updating and execution.

Figure 4A:
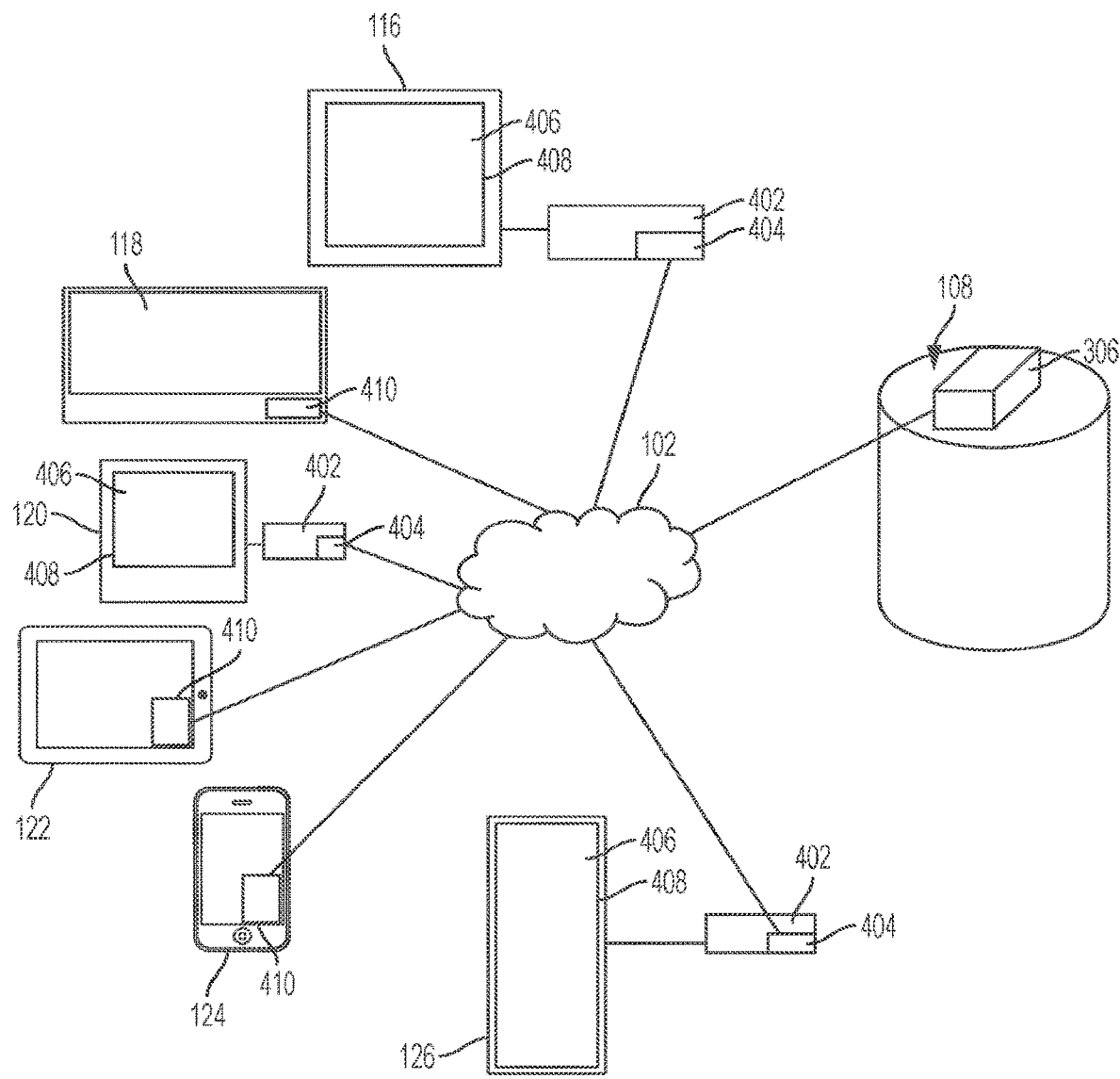
FIG. 4A illustrates another aspect of an interactive communications and control system within a healthcare institution, and devices utilized in that system, as shown and described herein.

Referring now to FIG. 4A, another aspect of the system 100 is shown. Here, the system 100 includes various user, or endpoint, devices configured to allow end users (for example, patients, family members of patients, and healthcare institution personnel) to interact with and otherwise utilize the system 100.

The user devices can be in the form of a television 116, bedside terminal 120, and a dedicated digital white board terminal 126, each with an attendant television program box 402. In this embodiment, each television program box 402 is configured to store an executable program 404 that interfaces with the system application program 306 and allows the system application program 306 to communicate with the referenced devices and display the system's graphical user interface 406 on the display 408 of each device. It will be understood that with respect to the white board terminal 126, that terminal is configured, in one embodiment, to display key updated patient information on an ongoing basis in real time.

Similarly, the system 100 can also utilize a smart television 118, smart phones 124, smart tablets 122, or other intelligent devices that store an executable program 410 built into or otherwise stored upon each device, obviating the need for a program box such as program box 402 containing program 404.

In this embodiment, the executable programs 410 are configured to interface with the system application program 306 over the network 102 and allow the system application program 306 to communicate with the smart devices 118, 122 and 124 and display the system's graphical user interface 406 on the display 408 of each of the smart devices 168, 170 and 172.

It will be understood that the executable programs 404, 410 operating on or in conjunction with each user device are configured to also receive user input, such that each user of each device can input information actively (e.g., typing commands, selecting menu items, typing messages) or passively (e.g., tracked viewing habits), and provide (either sending or allowing access to) that information to the system application program 306 over the local area network 102, such that the system application program 306 can utilize that information in accordance with the operation of the system 100 described herein.

At this stage, it will be understood that the executable program 410 operating on the smart television 118 is configured to request information from the application server 108, including, but not limited to, information shown on the menu of each display (e.g., medication data 204, nursing assessment data 206, orders and results data 208, diet orders data 201, patient education data 212, patient requests and feedback data 214, meal ordering data 216, HVAC data 218, patient friendly medication data 220, and other data 236). It will be understood that the executable program 410 operating on the smart television 118 is configured to display this information on the user interface 408 located on the display 408 of the smart television 118, as the patient navigates through the various menu items.

It will be further understood that the executable program 410 operating on the smart television 118 is also configured to send active and passive information to the application server. Examples of active information include user-generated information (e.g., patient requests and feedback, meal ordering, HVAC requests) and passive user information (e.g., the time amount of a particular video a patient has watched, how many videos the patient has watched, how engaged is the patient with the various menu items in the system).

Figure 4B:
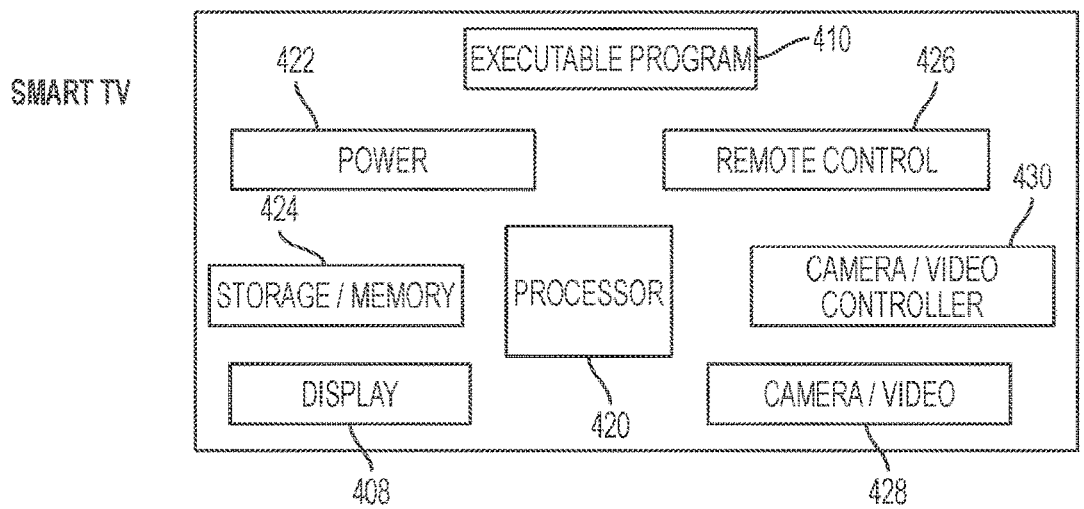
FIG. 4B illustrates another aspect of devices utilized by an interactive communications and control system within a healthcare institution, as shown and described herein.

Referring now to FIG. 4B, further description of the components of a smart television 118 is shown. In this embodiment, the smart television 118 includes a number of components including, but not limited to, a display 408, executable program 410, processor 420, power supply (battery or hardwire) 422, storage memory component 424, remote control controller 426, camera (two-way video and audio capability) 428, and camera-video controller 430. It will be understood that these are examples of components utilized with the system 100, but it will be further understood that the smart television 118 can include any number of other components that can be utilized by the system 100 in the manners described herein and otherwise.

The executable program 410, tools, and APIs are stored on the device (e.g. smart television 118) allowing the executable program 410 to communicate with and control the device (including the device hardware components (e.g., to turn the device 118 on/off)). This executable program 410 for each device has the ability to recognize the device type (in this case a smart television 118) and apply the appropriate controls. The executable program 410 is configured to load/reload from the application server 108 for various activity including, but not limited to, patient admission and discharge, and other roadmaps specific to the healthcare industry, and to have constant communication with the rest of the system 100.

Figure 4C:
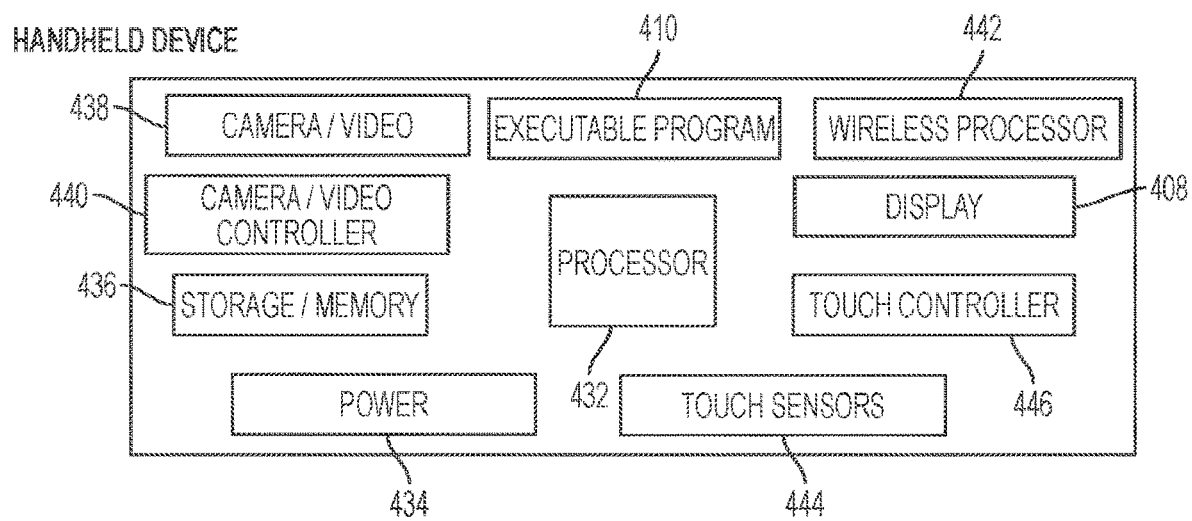
FIG. 4C illustrates another aspect of devices utilized by an interactive communications and control system within a healthcare institution, as shown and described herein.

Referring now to FIG. 4C, further description of the components of a mobile phone 124 or tablet 122 devices is shown. In this embodiment, mobile phone 124 and/or tablet 122 includes a number of components including, but not limited to, a display 408, executable program 410, processor 432, power supply (battery or hardwire) 432, storage memory component 436, camera (two-way video and audio capability) 438, and camera/video controller 440, wireless processor 442, touch sensors 444 and touch controller 446. It will be understood that these are examples of components utilized with the system 100, but it will be further understood that the mobile phone 124 or tablet 122 devices can include any number of other components that can be utilized by the system 100 in accordance with the manners described herein and otherwise.

It will be further understood that each of the system 100 components contains non-transient computer readable storage mediums, or other storage mediums, on which such components are capable of storing information including executable and non-executable computer code, related source code, course code, binary files, application program interfaces (APIs), and/or other executable code or instructions.

It will be further understood that communication between any or all of the system 100 components can be performed through operation of one or more application program interfaces (APIs) contained within the system 100 allowing communication between system 100 components over a local area network 102, or wide area network when accessing components or information residing outside of the facility.

It will be further understood that the server arrangements described herein are provided as examples, but the arrangement of servers could be made in a multitude of other ways, including through one or more additional virtual machine servers with storage memory components operating within a cloud-based server network, and/or other server arrangements that would allow the system 100 to operate in the manners described herein.

It will be understood that the system's 100 utilization of virtual servers to operate the system 100 as described herein, in combination with the integration program 228, application program 306, and other components and applications of the system 100, provides the system 100 with many significant enhancements.

For example, this configuration, as described herein, provides the system 100 with the enhanced ability to operate within a broad range of diverse host environments and datacenters. It also provides the system 100 with enhanced disaster recovery, uptime and scalability. It also reduces the institution's data center footprint and allows for server consolidation. It also provides for easier maintenance, including enhanced ability to install a virtual machine server from an existing copy/template, re-installing, backup and movement to a different server. It also allows for maintaining scaled down test systems, and applying security patches in compliance with the policies of each institution.

It also eliminates the need to supply hardware on site, and provides a specialized information system unique to the healthcare industry (eliminating the need to adapt applications built to serve datacenter infrastructure of other industries, such as the hotel industry). It also eliminates the need to draw from disparate hardware and software sources and third party proprietary equipment to operate the system 100. It also allows for easier management and integration of endpoints (e.g., devices such as tablets, cell phones, televisions, etc.).

Moreover, it also eliminates the need to use specific video streaming hardware and rely on third party video streaming vendors. It also and allows the system 100 to use newer technologies that support lower and variable bandwidth for display on different types of portable devices, which further allows for a greater number of simultaneous video streams and hence serve a larger number of rooms/beds. It also provides the flexibility to separate out components to the local facility per the requirements of each institution (for example, in a typical deployment, a video streaming server is placed at a local facility, which saves on video bandwidth over the wide area network, or the system could flex between streaming video from the datacenter and local facility based on availability). It will be understood that these are examples of enhancements that the current invention provides to the computer technology previously utilized for such applications, and that other enhancements also exist inherently or otherwise.

Referring now to FIG. 5A-5J, several embodiments of the user interface 406 displayed by the system application program 306 on each user device is shown. In these embodiments various menu items appear to a given user. In FIGS. 5A-F, these menu items and other offerings on the user interface 406 represent an entire feature set 501, providing the user with a multitude of offerings within the user interface 406.

It will be understood that one example of a feature set could be all of the elements and menu offerings shown and described in connection with FIGS. 5A-5F, and could also include many other features offered to a patient through the user interface 406 viewable on the display of the terminal or device. In the embodiments of FIGS. 5A-5F, the user can select actionable menu items in any manner allowed by the subject device, including, but not limited to, selection through remote control (such as through a television), selection through haptic contact engagement (such as through contact on the display of a smart phone or smart tablet), or selection through point-and-click (such as through a computer mouse and computer).

Figure 5A:
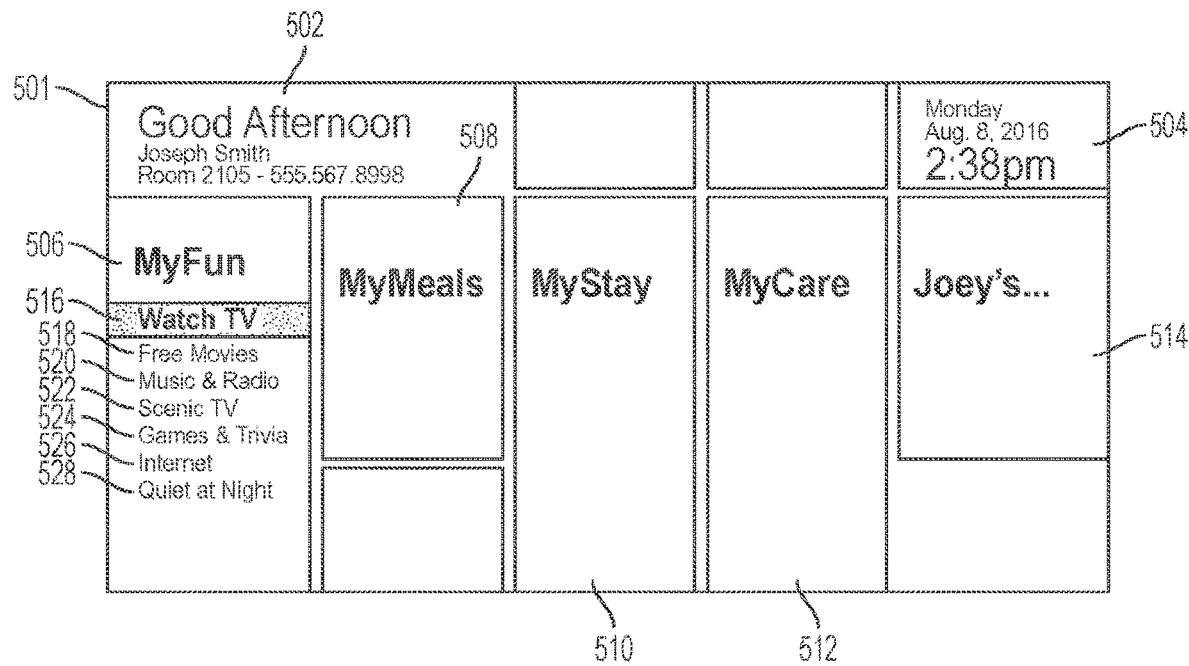
FIG. 5A illustrates a user interface utilized by an interactive communications and control system within a healthcare institution, as shown and described herein.
Figure 5B:
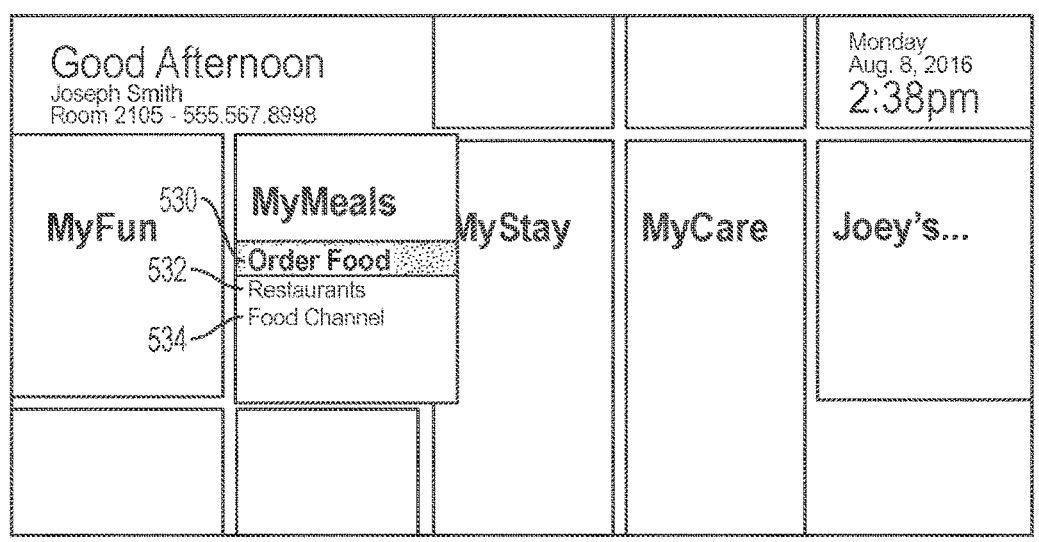
FIG. 5B illustrates another aspect of a user interface utilized by an interactive communications and control system within a healthcare institution, as shown and described herein.
Figure 5C:
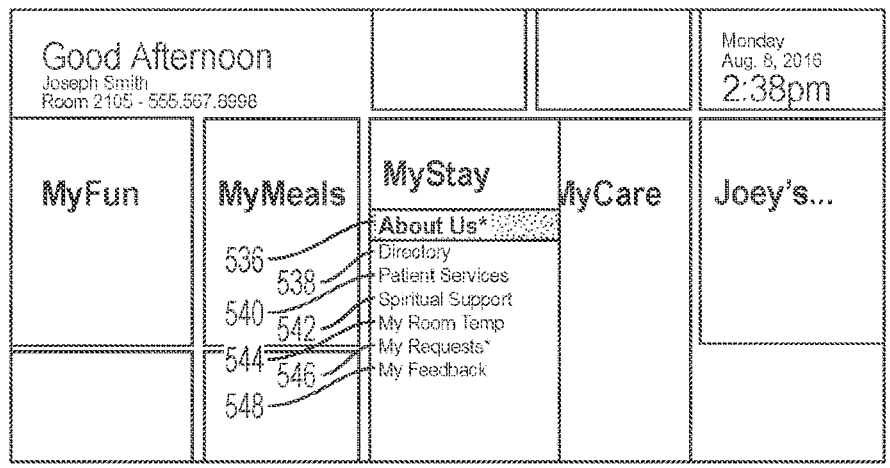
FIG. 5C illustrates another aspect of a user interface utilized by an interactive communications and control system within a healthcare institution, as shown and described herein.
Figure 5D:
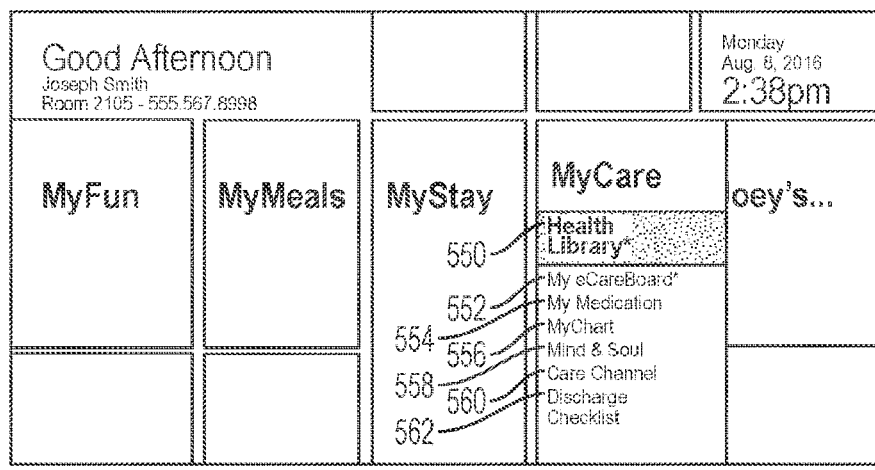
FIG. 5D illustrates another aspect of a user interface utilized by an interactive communications and control system within a healthcare institution, as shown and described herein.
Figure 5E:
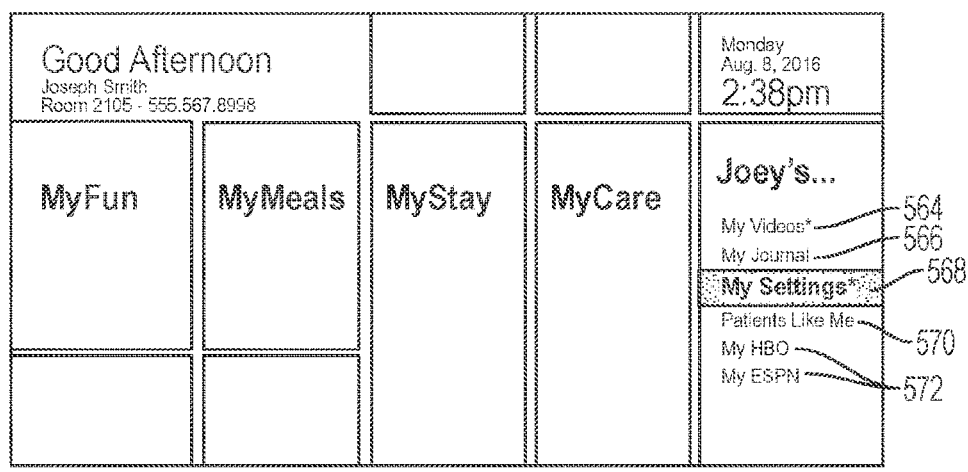
FIG. 5E illustrates another aspect of a user interface utilized by an interactive communications and control system within a healthcare institution, as shown and described herein.
Figure 5F:
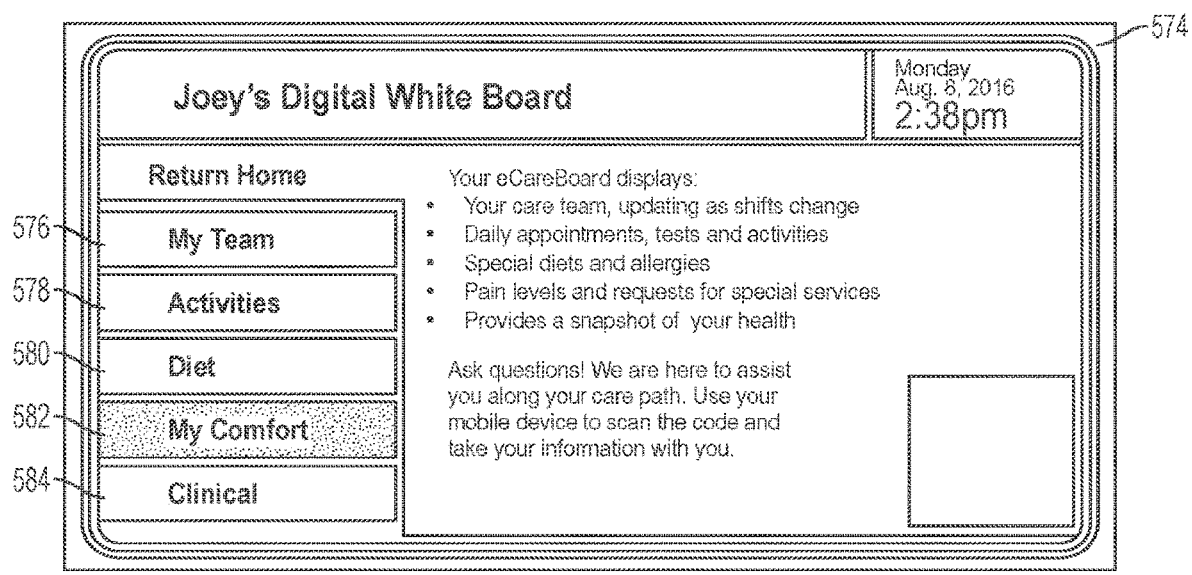
FIG. 5F illustrates another aspect of a user interface utilized by an interactive communications and control system within a healthcare institution, as shown and described herein.
Figure 5G:
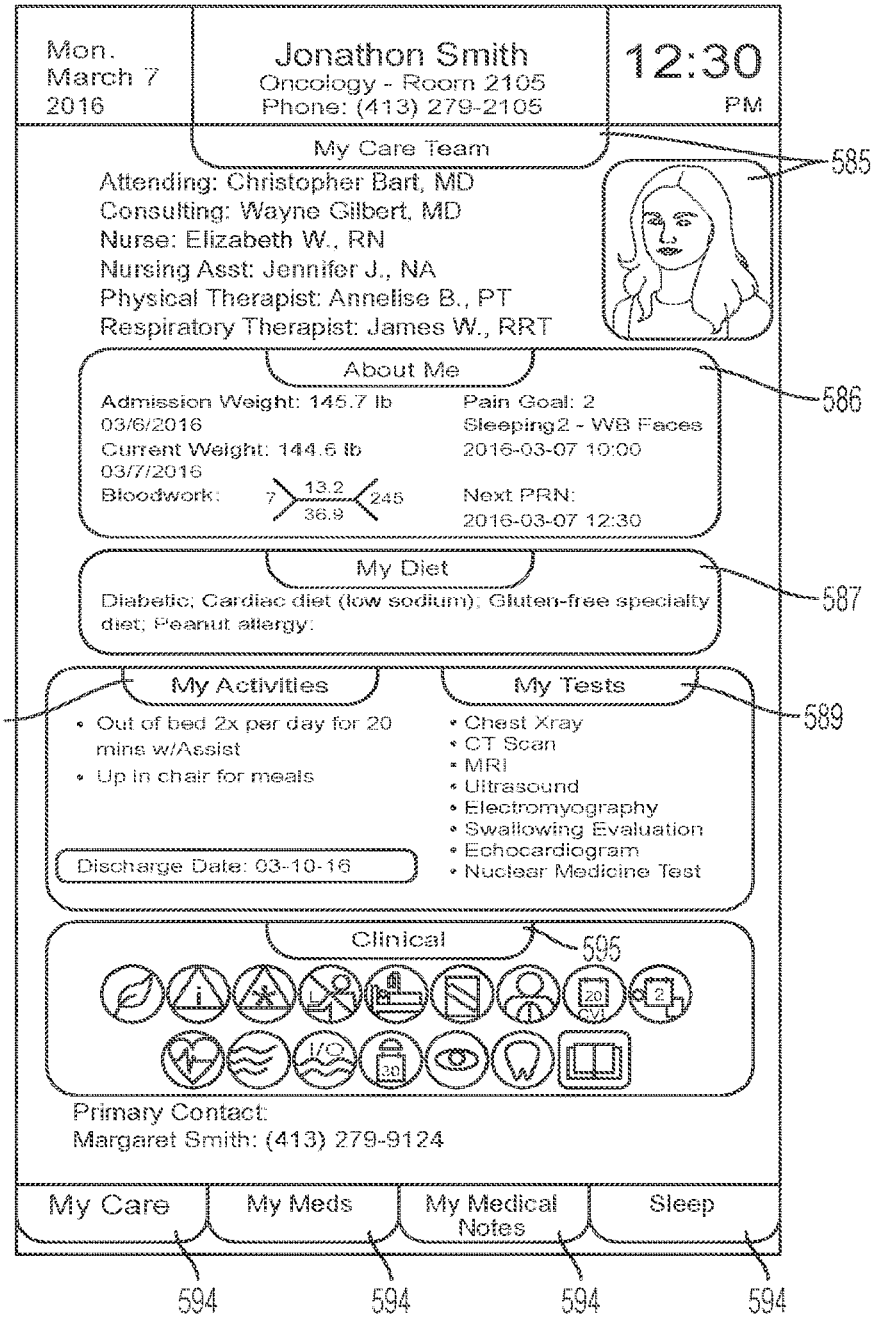
FIG. 5G illustrates another aspect of a user interface utilized by an interactive communications and control system within a healthcare institution, as shown and described herein.
Figure 5I:
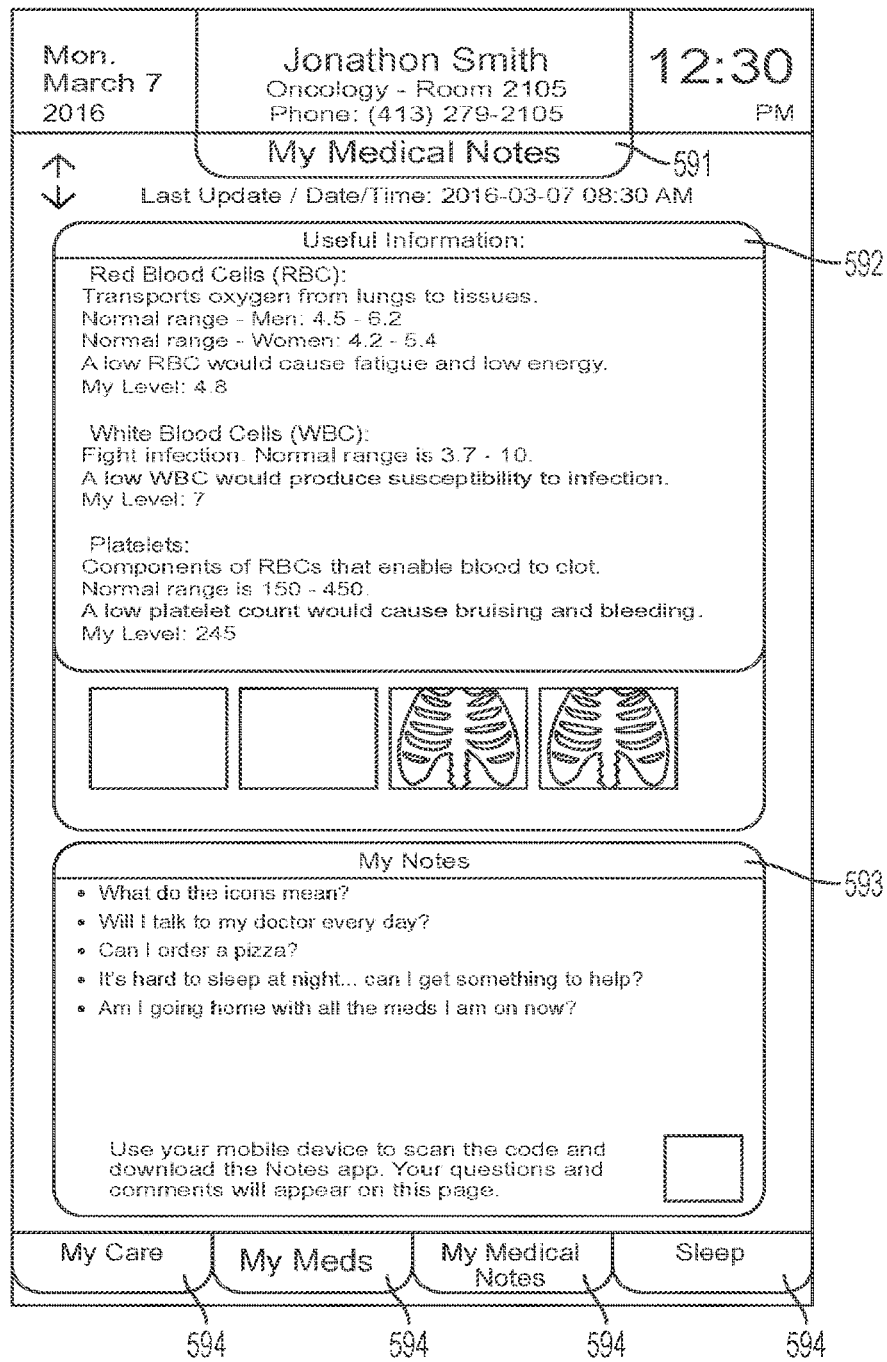
FIG. 5I illustrates another aspect of a user interface utilized by an interactive communications and control system within a healthcare institution, as shown and described herein.

With respect to FIGS. 5G-5I, an embodiment of a graphical user interface 406 for a digital white board 126 is shown. It will be understood that this information is designed to display key patient information in real time, and it utilized by the patient and healthcare professionals, and has distinct functionality from the feature set displayed by the user interfaces set out in 5A-5F.

Referring now to FIG. 5A, an embodiment of a system user interface 406 is shown. Here, patient name and room information 502 is displayed, along with the day, date and time 504. General menu items relating to enjoyment 506, meals 508, stay 510, care 512, and personalized information 514 are displayed. The enjoyment menu item 506 can have subset menu items for the patient to choose from including general television 516, free movies 518, scenic television 522, games and trivia 524, internet 526, and sleep-related content 528. It will be understood that once selected, each actionable menu item will direct the patient to a new page allowing that user to further interact with the system 100 with respect to subject matter relating to enjoyment.

Referring now to FIG. 5B, another embodiment of a system user interface 406 is shown. Here, the meals menu item 508 can have subset menu items for the patient to choose from including ordering food based on their diet restrictions 530, identifying local restaurants 532, and viewing content from designated food channels 534. It will be understood that once selected, each actionable menu item will direct the patient to a new page allowing that user to further interact with the system 100 with respect to subject matter relating to meals.

Referring now to FIG. 5C, another embodiment of a system user interface 406 is shown. Here, the stay menu item 510 can have subset menu items for the patient to choose from including key institution information 536, institution directory 538, patient services 540, spiritual support 542, room temperature 544, special requests 546, and patient feedback 548. It will be understood that once selected, each actionable menu item will direct the patient to a new page allowing that user to further interact with the system 100 with respect to subject matter relating to the patient's stay.

Referring now to FIG. 5D, another embodiment of a system user interface 406 is shown. Here, the care menu item 512 can have subset menu items for the patient to choose from including health education library 550, digital whiteboard 552, medication 554, patient-specific chart 556, mind and soul 558, care channel (relaxing content) 560, and discharge checklist 562. It will be understood that once selected, each actionable menu item will direct the patient to a new page allowing that user to further interact with the system 100 with respect to subject matter relating to care.

Referring now to FIG. 5E, another embodiment of a system user interface 406 is shown. Here, the personalized information menu item 514 can have subset menu items for the patient to choose from including specifically assigned educational videos 564, patient journal 566, system settings 568, analogous patient cases 570, and tailored entertainment 572. It will be understood that once selected, each actionable menu item will direct the patient to a new page allowing that user to further interact with the system 100 with respect to subject matter relating to personalized patient information.

Referring now to FIG. 5F, another embodiment of a system user interface 406 is shown. Here, a virtual white board interface 574 is shown, being displayed within the navigable user interface 406. Here, the information displayed includes detailed information concerning a patient's care team 576, daily appointments, tests and activities 578, special diets and allergies 580, pain levels and requests for special services 582, and medications, test results, and other clinical information 584.

Referring now to FIG. 5G, an embodiment of a system user interface 406 for a digital white board 126 is shown. Here, the information displayed includes detailed information concerning a patient's care team 585, physiology 586, diet 587, activities and schedule 588, tests 580, and other clinical information 595. Subject matter tabs 594 for each set of data are provided on the display of the digital white board 126.

Referring now to FIG. 5H, another embodiment of a system user interface 406 for a digital white board 126 is shown. Here, the information displayed includes detailed information concerning a patient's medication 590, which could be a variety of medications falling under different fields 596. Subject matter tabs 594 for each set of data are provided on the display of the digital whiteboard 126.

Referring now to FIG. 5I, another embodiment of a system user interface 406 for a digital white board 126 is shown. Here, the information displayed includes detailed information concerning key medical notes 591 for the patient, including a general category of useful clinical information 592, as well as other notes 593. Subject matter tabs 594 for each set of data are provided on the display of the digital white board 126.

Figure 6:
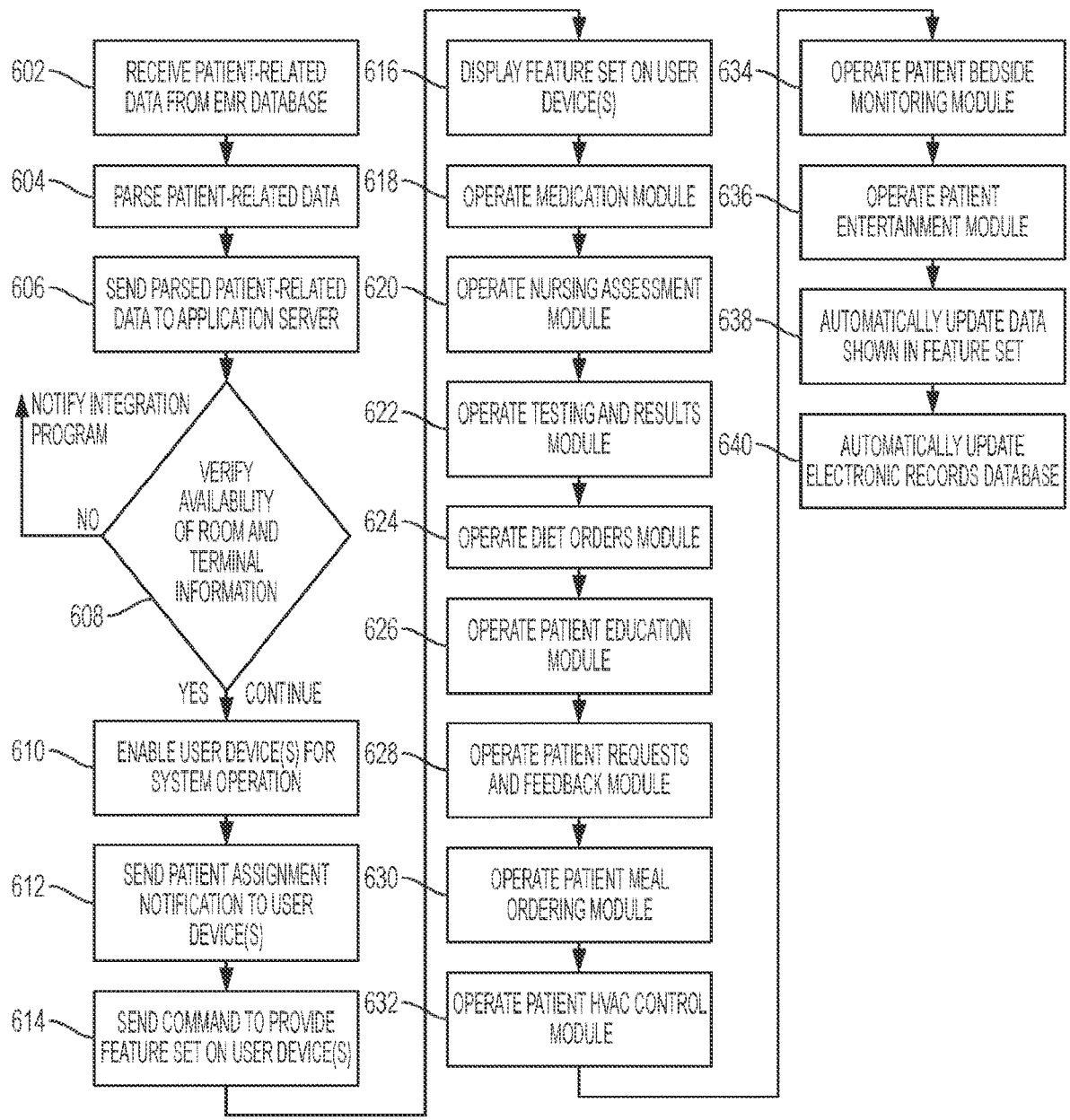
FIG. 6 illustrates a method for the interactive sharing of information within a healthcare institution, as shown and described herein.

Referring now to FIG. 6, an embodiment of an interactive sharing of patient-related information method 600 is shown.

In step 602 of method 600, the integration application program 228 operating on the integration server 106 receives the ADT data 202, medications data 204, nursing assessment data 206, orders and results data 208, diet ordering data 210, education data 212, patient requests and feedback data 214, meal ordering data 216, HVAC (temperature control) data 218, patient friendly medication data 220, and other data 236 from the institution's EMR system 104.

In step 604 of method 600, the integration application program 228 operating on the integration server 106 parses the ADT data 202, medications data 204, nursing assessment data 206, orders and results data 208, diet ordering data 210, education data 212, patient requests and feedback data 214, meal ordering data 216, HVAC (temperature control) data 218, patient friendly medication data 220, and other data 236.

In step 606 of method 600, the integration application program 228 operating on the integration server 106 sends the parsed ADT data 202 to the application server 108. It will be understood that the ADT data 202 includes admission, discharge, transfer, and room information for each patient, as well as other patient data including, but not limited to, the patient's name, identifying information, demographics, physicians assigned to the patient, and other relevant information for that patient. The integration application program 228 passes all of this information to the application server 108 and the application server 108 stores that information as part of the patient's record.

In step 608 of method 600, the system application program 306 operating on the application server 108 verifies whether the room identified in the parsed ADT data 202 for a given patient is available. If such room is available, the method 600 continues. If not, the system application program 306 notifies the integration application program 228 and the method 600 ceases until the ADT data 202 is updated or otherwise corrected and the method 600 commences again beginning at step 602. It will be understood that the terminals 120 and other in-room devices are associated with certain rooms and beds in the institution during the initial configuration of the system 100. If for some reason a terminal 120 or device is not properly associated with a certain room and bed, or is replaced, the system application program 306 will provide a message of "Service Not Available" viewable on the user terminal or device, until the terminal or device is properly assigned to the appropriate room and bed.

In step 610 of method 600, if verified, the system application program 306 operating on the application server 108 enables the one or more devices and/or terminals in the assigned room to receive and otherwise display the patient-related information from the system 100. In this embodiment, the method 600 will utilize a single smart television 118 assigned to a certain room for a certain patient. However, it will be understood that multiple devices configured to be utilized by the system 100 and users of the system 100 could also be used as a terminal or device component of the system 100 in the manner described herein.

In step 612 of method 600, the system application program 306 operating on the application server 108 sends or pushes a notification to the smart television 118 that a certain patient is assigned to that device.

In step 614 of method 600, the system application program 306 operating on the application server 108 sends or pushes a command to the smart television 118 that the smart television 118 make the appropriate feature set 501 available on the smart television 118 for that patient.

In step 616 of method 600, the executable program 410 operating on the smart television 118 displays the feature set 501 on the user interface 408 located on the display 408 of the smart television 118. It will be understood that the feature set 501 in this embodiment includes, but is not limited to, the feature set 501 shown and described in FIG. 5, including all menu items, date and time information, and other information that the system application program 306 operating on the application server 108 sends to and receives from the smart television 118 to populate and otherwise link to the menu items on the user interface 406 as the user operates the system 100.

It will be understood that with respect to other smart devices, such as smart phones 124 and smart tablets 122, such devices are configured to receive a verification code from the system 100 to confirm the device belongs to that patient and is allowed access. It will be further understood that such access will be restricted to the patient room only, and would not be allowed once the device is removed from the room through a combination of local WiFi or geo-location mechanism, in which case the smart phones 124 and smart tablets 122. could contain general information and media but no patient-specific information.

At this stage, it will be understood that the smart television 118 is now connected to and otherwise operational within the system 100. It will be further understood that any number of different methods exist in connection with the operation of the system with respect to each feature of the feature set 501. For example, the system components can be configured to operate certain modules of each feature set 501.

Figure 7:
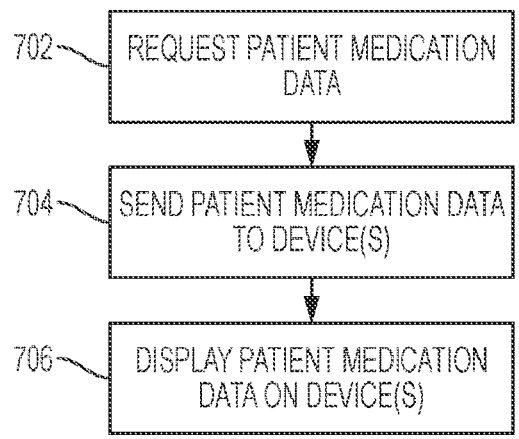
FIG. 7 illustrates another aspect of a method for the interactive sharing of information within a healthcare institution, as shown and described herein.

Accordingly, in step 618 of method 600, the system 100 operates a feature set based on medication data 204, more fully shown and described in reference to FIG. 7.

Figure 8:
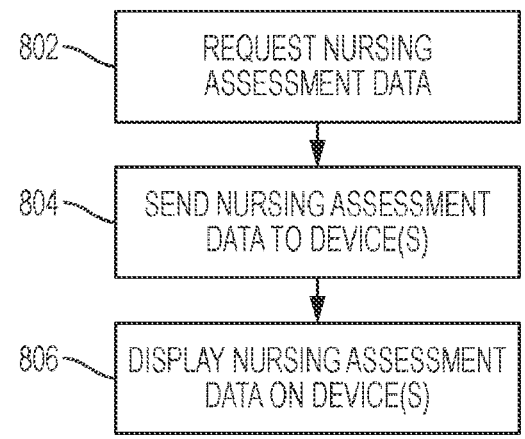
FIG. 8 illustrates another aspect of a method for the interactive sharing of information within a healthcare institution, as shown and described herein.

In step 620 of method 600, the system 100 operates a feature set based on nursing assessment data 206, more fully shown and described in reference to FIG. 8.

Figure 9:
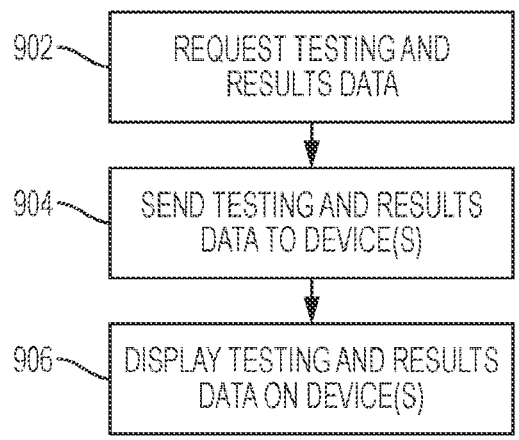
FIG. 9 illustrates another aspect of a method for the interactive sharing of information within a healthcare institution, as shown and described herein.

In step 622 of method 600, the system 100 operates a feature set based on orders and results data 208, more fully shown and described in reference to FIG. 9.

Figure 10:
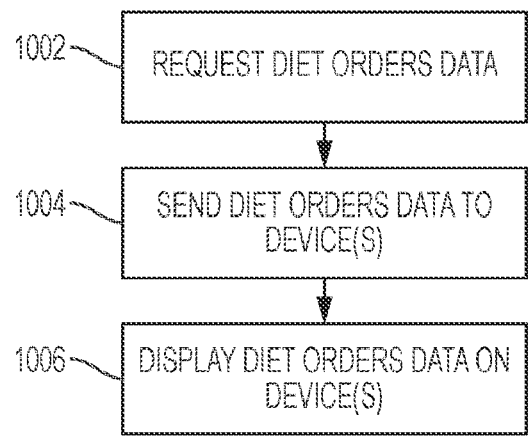
FIG. 10 illustrates another aspect of a method for the interactive sharing of information within a healthcare institution, as shown and described herein.

In step 624 of method 600, the system 100 operates a feature set based on diet orders data 210, more fully shown and described in reference to FIG. 10.

Figure 11:
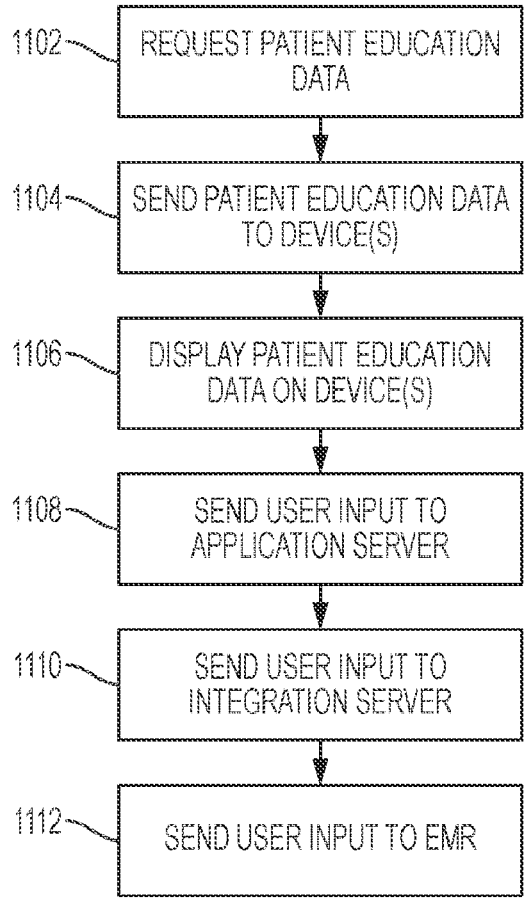
FIG. 11 illustrates another aspect of a method for the interactive sharing of information within a healthcare institution, as shown and described herein.

In step 626 of method 600, the system 100 operates a feature set based on patient education data 212, more fully shown and described in reference to FIG. 11.

Figure 12:
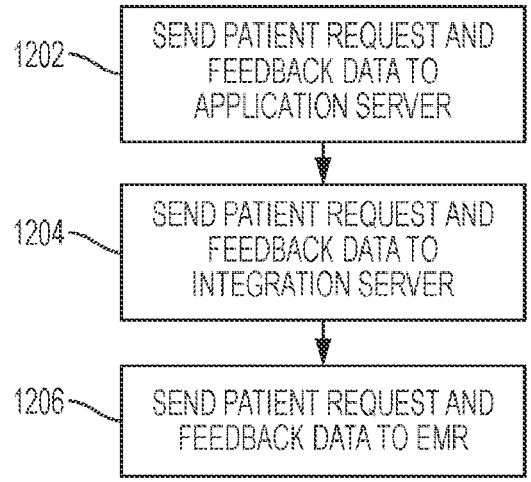
FIG. 12 illustrates another aspect of a method for the interactive sharing of information within a healthcare institution, as shown and described herein.

In step 628 of method 600, the system 100 operates a feature set based on patient requests and feedback data 214, more fully shown and described in reference to FIG. 12.

Figure 13:
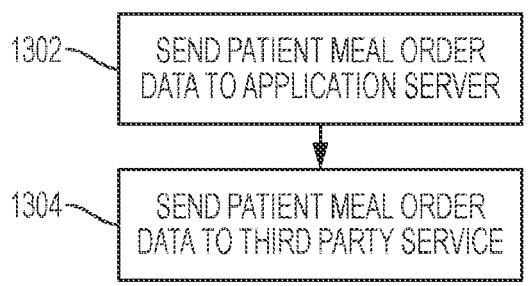
FIG. 13 illustrates another aspect of a method for the interactive sharing of information within a healthcare institution, as shown and described herein.

In step 630 of method 600, the system 100 operates a feature set based on patient meal ordering data 216, more fully shown and described in reference to FIG. 13.

Figure 14:
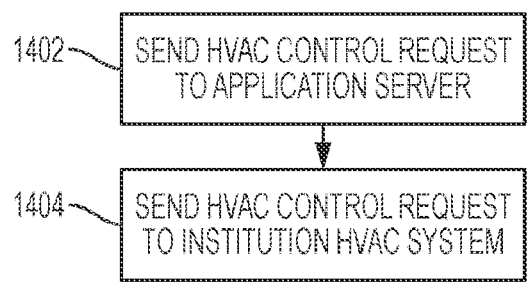
FIG. 14 illustrates another aspect of a method for the interactive sharing of information within a healthcare institution, as shown and described herein.

In step 632 of method 600, the system 100 operates a feature set based on patient HVAC control requests 218, more fully shown and described in reference to FIG. 14.

In step 634 of method 600, the system 100 operates a feature set based on patient bedside monitoring requests, more fully shown and described in reference to FIG. 15.

In step 636 of method 600, the system 100 operates a feature set based on patient entertainment, more fully shown and described in reference to FIG. 16.

In step 638 of method 600, the information contained in each feature set 501 described herein is continually updated as each of the feature set 501 menu items and other items are accessed. It will be understood that the updating of the underlying data occurs automatically based on communication between the various system components, including between the application server 108, integration server 106, and facility EMR system 104.

In step 640 of method 600, the information contained in the facility EMR system 104 is continually updated based on information received from the integration program 228 operating on the integration server 106 (based on information received from other system 100 components including the application server 108) based on certain activities by the patient.

It will be further understood that the modules described herein are provided as examples, and that other modules and features could also be understood by one of ordinary skill in the art to be within the scope of the invention as described herein.

Referring now to FIG. 7, steps for a medication data module of the present invention is shown and described in accordance with method 700. In step 702 of method 700, the executable program 410 operating on the smart television 118 requests patient medication data 204 from the application server 108 as a result of the user selection of the medication menu item 554.

In step 704 of method 700, the system application program 306 operating on the application server 108 sends the patient medication data 204 to the smart television 118. It will be understood that the integration program 228 operating on the integration server 106 parses the medication data 204 orders received from the EMR system 104 for key identifying information that is then used to query systems from other vendors to obtain, parse and store patient-friendly information. The integration program 228 operating on the integration server 106 sends this information to the application server 108. The application program 306 operating on the application server 108 sends the patient medication data 204 to the smart television 118 for display on the user interface 406 on the in-room device. Other activities such as immediate discontinuation of certain medications, updates to discontinuation dates in the future, and other key information items relating to patient medication data 204 are updated and/or modified in the the system 100 accordingly.

In step 706 of method 700, the executable program 410 operating on the smart television 118 displays the medication data 204 on the display 408 of the smart television 118.

Referring now to FIG. 8, steps for a nursing assessment data module of the present invention is shown and described in accordance with method 800. In step 802 of method 800, the executable program 410 operating on the smart television 118 requests nursing assessment data 206 from the application server 108 as a result of the user selection of the nursing assessment data from the care menu item 512.

In step 804 of method 800, the system application program 306 operating on the application server 108 sends the nursing assessment data 206 to the smart television 118. It will be understood that the nursing assessment data 206 includes, but is not limited to, nursing assessments and documentation including patient activity, goals, pain scale, and other data.

It will be further understood that the integration program 228 operating on the integration server 106 evaluates and acts upon the nursing assessment data 206 received from the EMR system 104. This includes assessment of the type of information received from the EMR system 104, updating the patient's clinical records within the system 100 appropriately, referencing patient friendly text as well as visual cues (fall risk, hearing aid, etc.) that is extensively mapped in the system 100 and database 110 design along with rules to handle updates for the different types of activity generated. For certain institutions, EMR systems 104, staff assignments and shifts might also be part of these records.

In step 806 of method 800, the executable program 410 operating on the smart television 118 displays the nursing assessment data 206 on the display 408 of the smart television 118. It will be understood that the nursing assessment data 206, as well as other patient-related data referenced herein, including in connection with FIGS. 5G, H and I, can also be displayed on the digital white board 126. In that configuration, the system application 306 operating on the application server 108 causes the information displayed on the digital white board 126 to be updated automatically in red time based on information changes at the EMR system level 104.

Referring now to FIG. 9, steps for an orders and results data module of the present invention is shown and described in accordance with method 900. In step 902 of method 900, the executable program 410 operating on the smart television 118 requests orders and results data 208 from the application server 108 as a consequence of the user selection of the orders and results data 208 from the care menu item 512.

In step 904 of method 690, the system application program 306 operating on the application server 108 sends the orders and results data 208 to the smart television 118. It will be understood that the orders and results data 208 includes, but is not limited to, data relating to orders for patients such as radiology (X-Rays, CT scans, MRIs), cardiology (ECG), and laboratory tests. It will be further understood that this information originates in the institution EMR system 104 and is parsed by the integration application program 228 and sent to and stored by the application server 108, such that the application program 306 operating on the application server 108 can send the data to the smart television 118 in accordance with the invention as described herein.

In step 906 of method 900, the executable program 410 operating on the smart television 118 displays the orders and results data 208 on the display 408 of the smart television 118.

Referring now to FIG. 10, steps for a diet orders data module of the present invention is shown and described in accordance with method 1000. In step 1002 of method 1000, the executable program 410 operating on the smart television 118 requests the diet orders data 210 from the application server 108 as a result of the user selection of the diet orders data 210 from the meals menu item 508.

In step 1004 of method 1000, the system application program 306 operating on the application server 108 sends the diet orders data 210 to the smart television 118. It will be understood that the diet orders data 210 includes, but is not limited to, recommended or required diet order from healthcare personnel based on a patient's condition (e.g., "no eating for 12 hours before surgery," "no sugar," "fluids only"). It will be further understood that diet orders data 210 received from the EMR system 104 can have certain codes that are mapped to patient friendly information within the system 100. The application program 306 operating on the application server 108 looks up these codes and stores these codes against the patient's clinical information for display on the user interface 406 on the in-room device.

In step 1006 of method 1000, the executable program 410 operating on the smart television 118 displays the diet orders data 210 on the display 408 of the smart television 118.

Referring now to FIG. 11, steps for patient education feature of the present invention is shown and described in accordance with method 1100. In step 1102 of method 1100, the executable program 410 operating on the smart television 118 requests patient education data 212 from the application server 108 as a result of the user selection of patient education data 212 from the personalized information menu item 514.

In step 1104 of method 1100, the system application program 306 operating on the application server 108 sends the requested patient education data 212 to the smart television 118. It will be understood that the data 212 is available to the system application program 306 because the integration program 228 operating on the integration server 106 continually receives relevant education data 212 from the EMR system 104, parses that data, and automatically sends that parsed data to the application server 108.

It will be further understood that the patient education feature of the system 100 is functionally bi-directional. For example, patient education data 212 (including videos, articles, and other information) can be initiated by institution professionals and staff at the EMR system 104 level. In putting the education data 212 together, institution professionals can draw from multiple sources including, but not limited to, physician orders, problem lists, medications, educational videos, and other sources.

It will be further understood that patient education data 212 content to be viewed (e.g., an educational video) is mapped in the system 100 along with questions on who is going to view the content and followed by questions to document patient comprehension. It will be further understood that the patient education data 212 can be provided in the form of educational video packets, or highly customized, prepared and vetted video and/or textual information relating to the specific condition, procedure, or other health-related item specifically relating to each patient, to be provided to each patient at the proper time.

In step 1106 of method 1100, the executable program 410 operating on the smart television 118 displays the patient education data 212 on the display 408 of the smart television 118. It will be understood that when a patient views the appropriate patient education data 212 content through the user interface 406, information relating to that viewing (e.g., if a video, whether viewing of a video was completed, and if not, how long the video was viewed) is passed back to the application server 108.

In step 1108 of method 1100, the executable program 410 operating on the smart television 118 sends the user input relating to the patient education data 212 to the application server 108.

In step 1110 of method 1100, the system application program 306 operating on the application server 108 sends the user input relating to the patient education data 212 to the integration server 106 where the proper message format is created in the interface engine 230.

In step 1112 of method 1100, the integration application program 228 operating on the integration server 106 sends the user input relating to the patient education data 212 to the EMR system 104 for documentation.

Referring now to FIG. 12, steps for a patient requests and feedback of the present invention is shown and described in accordance with method 1200. In step 1202 of method 1200, the executable program 410 operating on the smart television 118 sends patient requests and feedback data 214 to the application server 108 as a result of the user sending such data through the appropriate user menu item.

In step 1204 of method 1200, the system application program 306 operating on the application server 108 sends the patient requests and feedback data 214 to the integration server 106 where the proper message format is created in the interface engine 230.

It will be understood that the patient requests and feedback data 214 are messages that result from a patient selecting an item on the user interface 406 and are sent from there to the application server 108 which stores relevant information and sends that information to the integration server 106. It will be further understood that patient requests include, but are not limited to, any number of patient requests, such as wanting to speak to a pharmacist, wanting to speak with clergy, wanting a pillow, requesting bedside delivery of discharge medications, and the like. Requests such as for bedside delivery of discharge medications might be formatted as orders or results messages and sent back to the EMR system 104 for documentation and appropriate action. Similarly patient feedback, surveys, service recovery can be reported in a variety of formats to messaging systems and/or applications (like Vocera), or email, text message, and the like.

In step 1206 of method 1200, the integration application program 228 operating on the integration server 106 sends the patient requests and feedback data 214 to the EMR system 104 so that appropriate action can be taken.

Referring now to FIG. 13, steps for a patient meal ordering data module of the present invention is shown and described in accordance with method 1300. In step 1302 of method 1300, the executable program 410 operating on the smart television 118 sends patient meal orders 216 to the application server 108 as a result of the user sending requesting such meal orders 216 through the user meals menu 508.

In step 1304 of method 1300, the system application program 306 operating on the application server 108 sends the patient meal orders 216 to a third party food service interface. It will be understood that such web-based food services provide dietary and nutrition services and systems to a given institution. The display and categorization of meals can be designed for each user interface 406 for each institution. In this embodiment, as the patient navigates the user interface 406, meals specific to the patient's diet are dynamically obtained through the user interface 406 and rules and restrictions are computed before the patient makes the final selection that is then passed back to the appropriate dietary and nutrition services and systems.

Referring now to FIG. 14, steps for a patient HVAC control module of the present invention is shown and described in accordance with method 1400. In step 1402 of method 1400, the executable program 410 operating on the smart television 118 sends patient HVAC control requests 218 to the application server 108 as a result of the user sending such HVAC control requests 218 (e.g., increase room temperature) through the stay menu item 510.

In step 1404 of method 1400, the system application program 306 operating on the application server 108 sends the patient HVAC control requests 218 data to the institution HVAC system. It will be understood that the integration server 106 communicates with the application server 108 when ADT data 202 messages are received to request room temperatures be set to default values.

Referring now to FIG. 15, steps for a patient bedside monitoring module of the present invention is shown and described in accordance with method 1500. In step 1502 of method 1500, the system application program 306 operating on the application server 108 receives a request for bedside monitoring from a third party video conferencing system.

In step 1504 of method 1500, the system application program 306 operating on the application server 108 sends a notification to the user interface 406 of the the smart television 118 to switch the smart television's 118 input to the appropriate source to receive the video conference. It will be understood that the user consent for this step is not required, and a device may be "hijacked" such that the healthcare professional can view the patient in a videoconferencing setting at any time the healthcare professional deems such a virtual visit is warranted. It will be further understood that additional components attached to the smart television 118 is configured to allow two-way audio and video communication between healthcare professional, patient, and patient guardians where applicable, through its various hardware and software features as shown and described herein.

In step 1506 of method 1500, the executable program 410 operating on the smart television 118 enables the videoconferencing to commence on the display 408 of the smart television 118.

In step 1508 of method 1500, the system application program 306 operating on the application server 108 sends a notification to the smart television 118 that the videoconference session has concluded.

In step 1510 of method 1500, the executable program 410 operating on the smart television 118 displays the original user interface 406 on the smart television 118.

Referring now to FIG. 16, steps for a patient entertainment module of the present invention is shown and described in accordance with method 1600. In step 1602 of method 1600, the executable program 410 operating on the smart television 118 displays the entertainment data 226 on the user interface 408 located on the display 408 of the smart television 118.

In step 1604 of method 1600, the system application program 306 operating on the application server 108 accesses system entertainment data 320 stored in the database server 110 per the patient's selection.

In step 1606 of method 1600, the system application program 306 operating on the application server 108 sends system entertainment data 226, stored in the system database 110, to the smart television 118.

In step 1608 of method 1600, the system application program 306 operating on the application server 108 utilized the streaming server 114 to allow for the seamless viewing of video entertainment data 226 on the user interface 408 located on the display 408 of the smart television 118.

It will be understood that although new data in the institution's EMR system 104 and elsewhere is updated across the relevant components of the system 100 databases as such new data is received, the typical process for displaying the updated information is to refresh such data on the specific screens of the user interface 406 that the patient is accessing.

Figure 17:
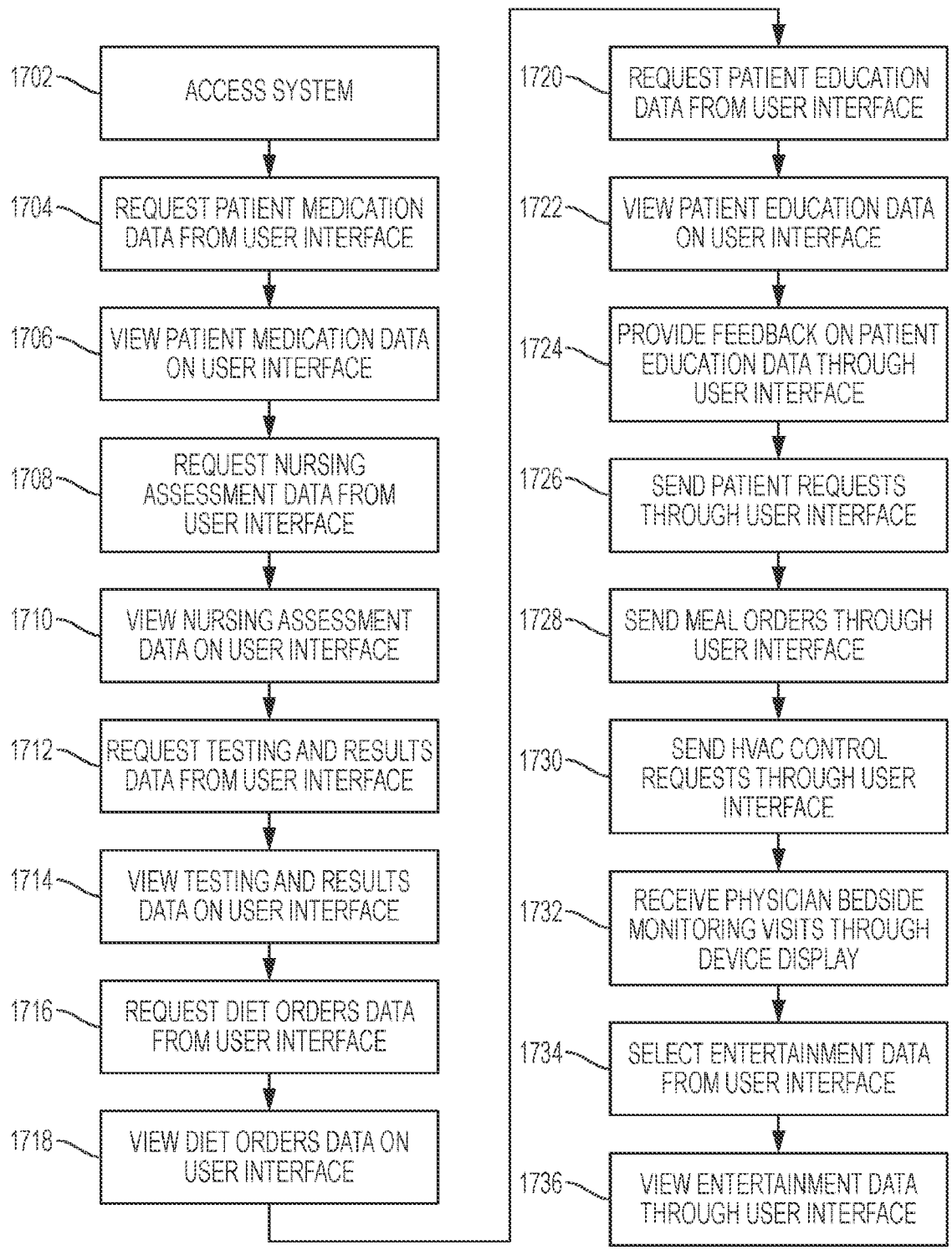
FIG. 17 illustrates a method for the interactive sharing of information within a healthcare institution, as shown and described herein.

Referring now to FIG. 17, an embodiment of an interactive sharing of patient-related information method 1700 is shown. It will be understood that, in this embodiment, the method is described from the perspective of the user of the system 100.

In step 1702 of method 1700, the user accesses the system 100 through a smart television 118 located in a patient room.

In step 1704 of method 1700, the user requests patient medication data 204 from a menu item located on the user interface 406 displayed on the smart television 118.

In step 1706 of method 1700, the user views the requested patient medication data 204 on the display 408 of the smart television 118.

In step 1708 of method 1700, the user requests nursing assessment data 206 from a menu item located on the user interface 406 displayed on the smart television 118.

In step 1710 of method 1700, the user views the requested nursing assessment data 206 on the display 408 of the smart television 118.

In step 1712 of method 1700, the user requests orders and results data 208 from a menu item located on the user interface 406 displayed on the smart television 118.

In step 1714 of method 1700, the user views the requested orders and results data 208 on the display 408 of the smart television 118.

In step 1716 of method 1700, the user requests diet orders data 210 from a menu item located on the user interlace 406 displayed on the smart television 118.

In step 1718 of method 1700, the user views the requested diet orders data 210 on the display 408 of the smart television 118.

In step 1720 of method 1700, the user requests patient education data 212 from a menu item located on the user interface 406 displayed on the smart television 118.

In step 1722 of method 1700, the user views the requested patient education data 212 on the display 408 of the smart television 118.

In step 1724 of method 1700, the user provides feedback relating to the requested patient education data 212 through user input menu items located on the user interface 406 on the display 408 of the smart television 118.

In step 1726 of method 1700, the user sends requests and feedback data 214 through selection of a menu item located on the user interface 406 displayed on the smart television 118.

In step 1728 of method 1700, the user sends meal orders 216 through selection of a menu item located on the user interface 406 displayed on the smart television 118.

In step 1730 of method 1700, the user sends HVAC control requests 218 through selection of a menu item located on the user interface 406 displayed on the smart television 118.

In step 1732 of method 1700, the user receives physician bedside monitoring visits through the display 408 of the smart television 118.

In step 1734 of method 1700, the user selects entertainment data 226 through selection of a menu item located on the user interface 406 displayed on the smart television 118.

In step 1736 of method 1700, the user views the requested entertainment data 226 on the display 408 of the smart television 118.

It will be understood that not all of the steps in the methods described herein are required, or must be performed in the order as described herein.

Figure 18:
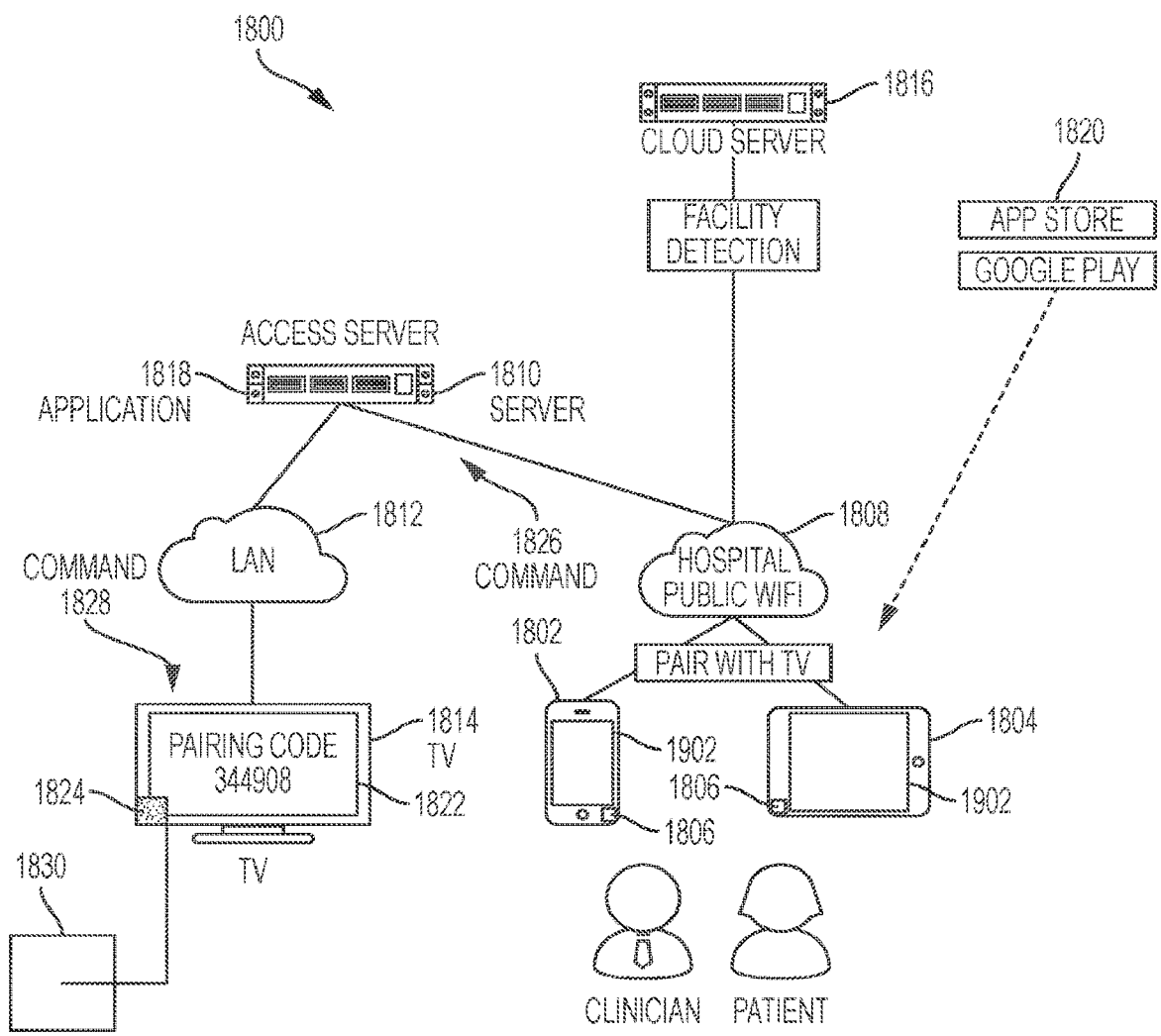
FIG. 18 illustrates a system for the control of media and communications systems, as shown and described herein.

Referring now to FIG. 18, an embodiment of a command-and-control system 1800 for the control of a media and communications system is shown.

The command-and-control system 1800 includes one or more types of user devices such as a mobile phone or tablet that performs many of the functions of a computer, typically having a touchscreen interface designed to be controlled through haptic contact engagement and an operating system capable of running downloaded applications, here shown as a smartphone device 1802 and a tablet device 1804.

The command-and-control system 1800 also includes other components including a wireless local area networking system 1808, a facility application control server 1810, a facility local area network 1812, a user display terminal such as a flat-screen television 1814 or other endpoint device, a mobile application server 1820, and a cloud server 1816. It will be understood that the system 1800 may include other components as necessary for the proper functioning of the system 1800.

Figure 19A:
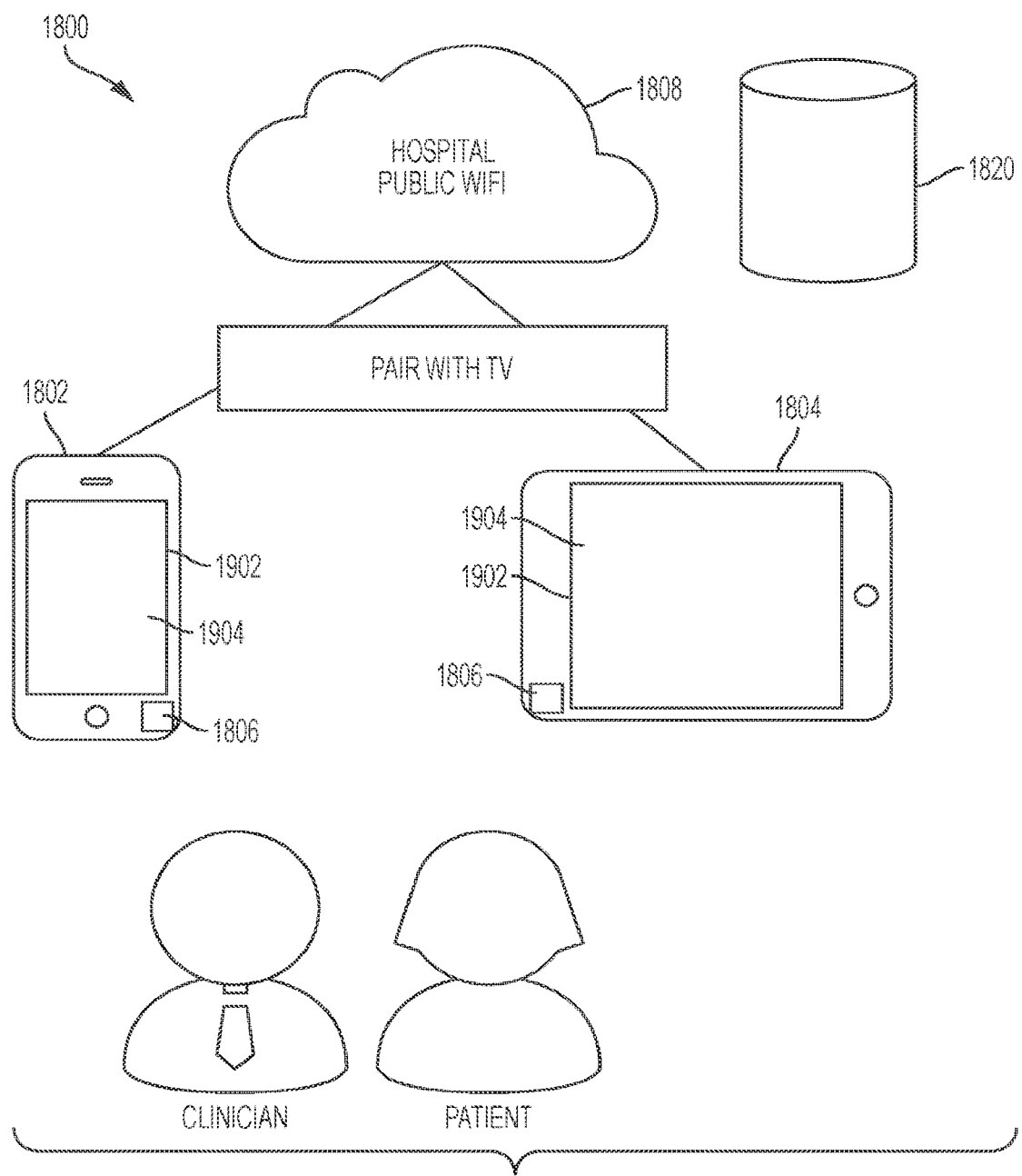
FIG. 19A illustrates another aspect of a system for the control of media and communications systems as shown and described herein.

Referring now to FIG. 19A, another aspect of the command-and-control system 1800 is shown. Here, the command-and-control system 1800 utilizes user devices 1802 and 1804, which are configured to allow end users (for example, clinicians, patients, and patient family members) to interact with and otherwise utilize the command-and-control system 1800. It will be understood that any number of other devices, in addition to smartphone device 1802 and tablet device 1804 can be utilized by the system, and that smartphone device 1802 and tablet device 1804 are being offered as examples herein.

In this embodiment, each device utilizes an executable mobile application program 1806, which is stored on each device 1802 and 1804. The mobile application program 1806 is downloaded onto each device 1802 and 1804 from a mobile application server 1820 (cloud-based or local), and each device 1802 and 1804 is periodically updated through real time Internet communications between the mobile application server 1820 and each device such as smartphone device 1802 and tablet device 1804.

The mobile application program 1806 includes one or more executable program files containing instructions to perform various operations allowing the user devices to properly interact with the system as shown and described herein. For example, when operating on each user device such as smartphone device 1802 and tablet device 1804, the mobile application program 1806 causes each user device to provide a user interface 1902 to each user, and, through the hardware and software configurations of such user devices 1802 and 1804, allow each user to control each user device through haptic contact engagement on the screens 1904 of each such device.

The mobile application program 1806 is also configured to communicate with the facility application control server 1810 over a wireless local area networking system 1808 such as WiFi (in accordance with standard 802.11 of the Institute of Electrical & Electronics Engineers (IEEE), as amended from time to time) to send and receive control commands 1826 and information, and to pair with the television 1814 or other end point device that is being controlled by the user.

The facility application program 1818 operating on the facility application server includes one or more executable program files containing instructions to perform various operations to operate the facility application. The facility application 1818 can be any number of applications including the systems and methods described in U.S. Provisional Application No. 62/420,945, or other facility, home or business media and communications systems.

The facility application program 1818 is configured to receive control commands 1826 and information from the mobile application programs 1806 operating on the user devices, such as smartphone device 1802 and tablet device 1804, and send commands 1828 directly to the endpoint device 1814.

The endpoint device 1814 has an endpoint device application program 1824 that includes one or more executable program files containing instructions to perform various operations to control the endpoint device 1814 and communicate with the facility application program 1818. The endpoint device application program 1824 is configured to receive commands 1828 from the facility application 1818 and control the content and navigation of what appears on the endpoint device 1814 display 1822. It will be understood that the endpoint device application program 1824 can be stored on an endpoint device control box 1830, or in another storage and control device or location, rather than on components located on or within the endpoint device 1814 itself.

It will be further understood that each of the command-and-control system 1800 components contains non-transient computer readable storage mediums, or other storage mediums, on which such components are capable of storing information including executable and non-executable computer code, related source code, course code, binary files, application program interfaces (APIs), and/or other executable code or instructions. It will be further understood that communication between any or all of the command-and-control system 1800 components can be performed through operation of one or more application program interfaces (APIs) located on or accessible through any of the system 1800 components, including in conjunction with any application programs stored or otherwise utilized by the system 1800.

Figure 19B:
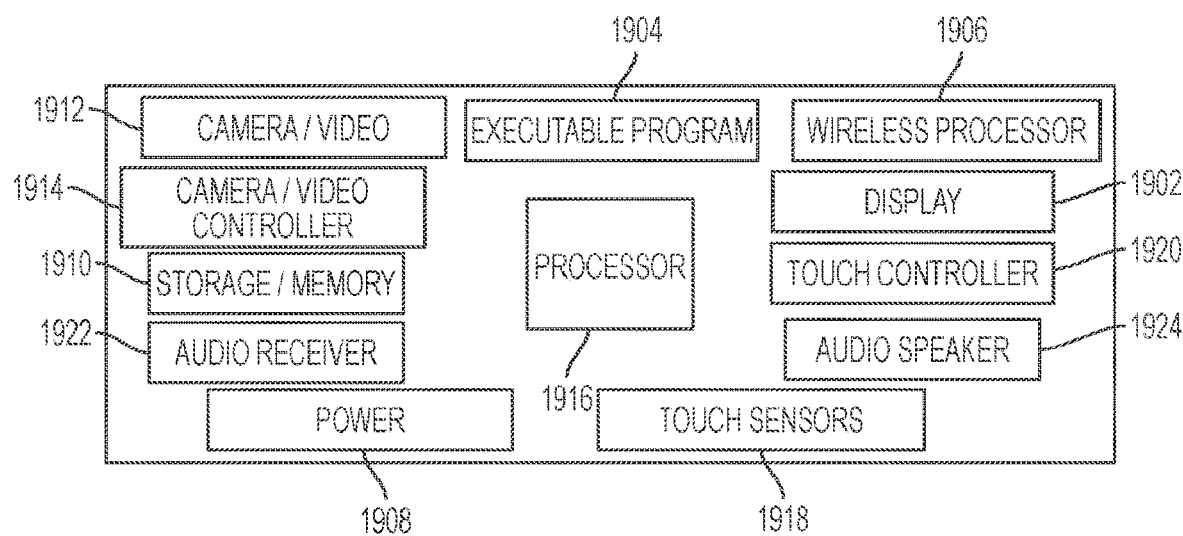
FIG. 19B illustrates another aspect of a system for the control of media and communications systems as shown and described herein.

Referring now to FIG. 19B, further details of the components of a smartphone device 1802 or tablet device 1804 are shown. In this embodiment, smartphone device 1802 and/or tablet device 1804 includes a number of components including, but not limited to, a display 1002, an executable program 1004, processor 1006, power supply (battery or hardwire) 1908, storage memory component 1910, camera (with two-way video and audio capability) 1912, and camera/video controller 1914, wireless processor 1916, touch sensors 1918, touch controller 1920, audio receiver 1922, and audio speaker 1924. It will be understood that these are examples of components utilized with the command-and-control system 1800, but it will be further understood that the smartphone 1802 or tablet 1804 devices can include any number of other components that can be utilized by the command-and-control system 1800 in accordance with the manners described herein and otherwise.

Figure 20:
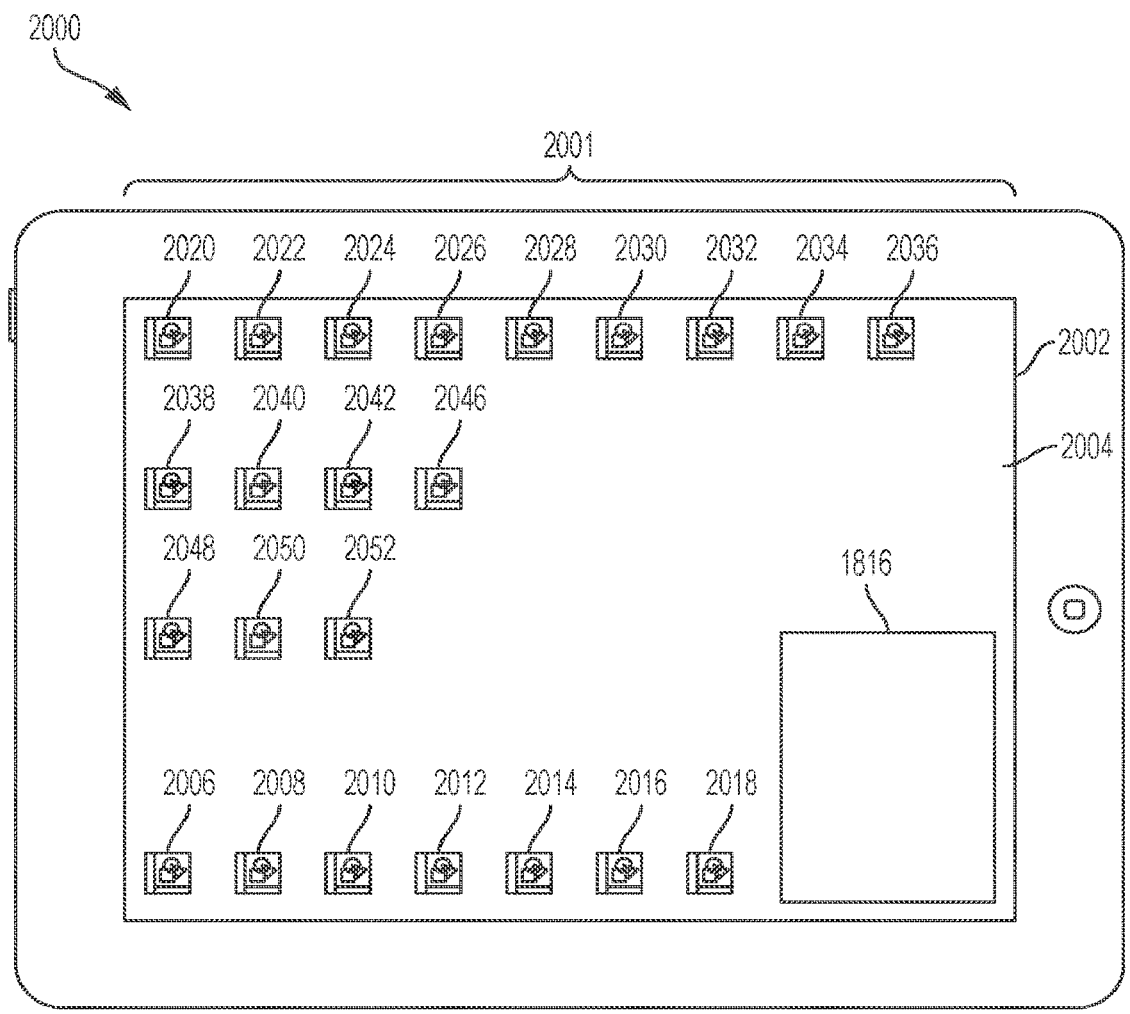
FIG. 20 illustrates another aspect of a system for the control of media and communications systems as shown and described herein.

Referring now to FIG. 20, further aspects of devices 1802 and 1804 are shown, here using tablet device 1804 to illustrate various control features. Tablet device 1802 has a display 2002, and the mobile application program 1806 operating on tablet device 1804 contains executable instructions to display a graphical user interface 2004 on the display 2002. The graphics and command icons displayed on the display 2002 can vary in terms of visual features and organizations, depending on how the mobile application program 1806 is programmed. Such display can be in menu format (with drop down options), icon format (with icons arranged in various ways on the display of the smartphone device 1802), or a combination of both.

In this embodiment, the graphical user interface 2004 provides various control icons 2001 visually displayed as icons on the interface 2004. Such control icons 2001 are provided to control the navigation among, and content of, what is being displayed on a television 1814 or other end point device screen 1822. Such control icons 2001 include, but are not limited to, an on/off control 2006 configured to control turning the endpoint device application program 1824 and/or endpoint device 1814 on or off; a search control 2008 configured to control the search function/magnifying glass where the user is allowed to type in words or letters and navigate more quickly within a particular screen or page having certain content, such as within an education library, movie category, or medication list shown on the endpoint device 1814 display 1822; a keyboard control 2010 configured to provide letters, numbers, page up/down, caps lock/shift, backspace/delete, enter, calculator, allowing the user to enter and send data to the facility application server 1810 through the facility application program 1818; a download control 2012 configured to provide a button (such as an arrow) that when clicked on (through haptic engagement) allows a user to download that particular information asset (such as a handout, pdf, video, or other information) from the application server 1810 or other server within the facility system; a mousepad control 2014 configured to allow haptic touch-application manipulation of the cursor on the screen, like a mouse would on a computer; and a swipe left/right control 2016 configured to allow the user to swipe to move from application to application being displayed, for example, on the endpoint device 1814, or quickly advance/scroll right/left through a number of information assets in a collection such as movies, education data, or other items.

Such control icons 2001 also include a scrolling up/down control 2018 configured to allow the user to quickly advance/scroll up/down through a number of information assets in a collection such as education titles or dietary items; a page up/down control 2020 configured to allow the user to quickly advance/scroll up/down (as above) through pages of information assets; a channel up/down control 2022 configured to allow the user to navigate the controls of the television 1814 or other end point device; an up/down, right/left and select arrows control 2024 configured to allow the user to incrementally move the focus of navigation and control 1 space up/down/left/right and choose it with the "select" button; an information button control 2026 configured to provide a button/icon such as a circled "I" that, when clicked on, would expand with more information, allowing the access and viewing of information on medications, dietary, movies, education, and other items, including program descriptions displayed on the smartphone device 1802 interface 2004 while viewing the content on the television 1814 or other end point device; and an information icon control 2028 which is configured to resemble the information button control 2026 but which is displayed on the television 1814 or other end point device screen 1822 (discretely at the bottom/side of the screen 1822) allowing, as with information button control 2026, the access and viewing of information on medications, dietary, movies, education, and other items, including program descriptions while viewing the content on the television 1814 or other end point device.

Such control icons 2001 also include a movie viewing control 2030 configured to provide commands/trick modes (e.g., Fast Forward, Rewind, Play/Pause, Stop, Save); a closed captioning control 2032 configured to provide several closed captioning options, toggling or turning on/off with the same button; a guide control 2034 configured to allow the user to go directly to the Electronic Programming Guide and display information about the television shows; a number keys control 2036 configured to provide channels, amounts (like in food ordering), and related items; a pointer control 2038 configured to allow the user to directly access certain area in the application or TV (banners, Information button, and related items; and a quick buttons control 2040 configured to provide users with access to popular features such as movies, dining, or home page.

Such control icons 2001 also include an exit control 2042 configured to allow the user to exit the application, movie, or other like application or content; a mute button control configured to allow the user to mute sound; a last control 2044 configured to allow the user to go directly to the last channel or could display list or graphics along bottom of screen showing "trail" of last viewed channels or applications; a favorites control 2046 configured to allow the user to manually access favorite channels/apps as entered by user or determined by most views; a home button control 2048 that allows the user to navigate to the home page of the respective application; an internet button control 2050 configured to allow the user to navigate to Internet (URL of choice); a settings control 2052 configured to allow the user to change device inputs, customize look of the application; and a data entry control 2054 configured to present a data entry box and keyboard to allow the user to put input notes or access a website.

It will be understood that the icons on the user interface 2004 can include all or a portion of the controls shown on the display of the endpoint device 1814. Thus, what is shown on the user interface 2004 is highly customizable based on the needs and desires of the institution or organization utilizing the system 1800. It will be under stood that what is in fact displayed to the user on the user interface 2004, particularly in terms of control icons, is determined by the device application programs 1806 operating on each user device, in coordination with lire facility application program 1818.

It will be further understood that the system 1800 is also configured to allow a user to navigate with his or her mobile device of choice (e.g., a smartphone device 1802, tablet device 1804, wearable, or other related items) in conjunction with, if desired, the traditional remote/pillow speaker, based on the needs of the user and/or institution. Thus, navigation could simultaneously be controlled with one paired device, e.g. smartphone device 1802, along with multiple unpaired devices, such as a pillow speaker or wireless remote.

It will be further understood that the system 1800 could also be configured to connect with Adaptive Devices such as sip/puff controls (that is, when a user sips on a straw or exhales into a tube as a way to provide commands into the system 1800); modularize certain components through a single button that brings up trick modes; and provide a "simplified" version with less features/functions to those who need less complex navigation, like Adaptive Devices such as sip/puff. For example, users with certain neurological handicaps (e.g. stroke or Parkinson's disease) may also use assistive technology to actuate the system.

It will be further understood that the system 1800 could also be configured to provide a Customer Relationship Management (CRM) component that would help clients use, manage and analyze (in a hospital setting) patient data throughout their relationship (inpatient and outpatient). An example use case is the ability to push previously stored patient preferences (e.g. entertainment, education, adaptive UI, language, "favorites"—either by frequency of user behavior or pre-defined by user) and adjust the user interface (UI). Another use case is recording and sending/storing patient device information (Operating System, phone number, email, credentials and related items) to hospital for follow-up/post discharge contact. It will be understood that collecting the above data can be a function of the endpoint device application, the mobile application program 1806, or integrated combination of of both.

It will be further understood that the system 1800 could also be configured to store and report on user activity (button clicks, quick buttons and related items) for continuous quality improvement of the application; run multiple applications in parallel (such as email, text, and the Internet), running on personal devices having button/icon for easy access; and have the ability to have more than one device control the television 1814 or other end point device or facility application program 1818, including the ability to allow a family member of a user (such as a patient in a healthcare facility) to navigate with his or her own device should the originally paired device lose battery charge or otherwise become inoperative because of malfunction, choice, or otherwise.

It will be further understood that the system 1800 could also be configured to allow users to personalize the user interface of each device in color or layout styles; "wipe"/purge data when leaving the institution (such as in a hospital/health care system environment); allow for voice commands and/or voice recognition to navigate and turn on/off, such as through a microphone button; provide the ability to be controlled in multiple languages, including voice recognition in user's chosen language; and allow for user devices to display a prompt to sync their device with the television 1814 or other end point device when within a predefined distance from the television 1814 or other end point device.

It will be understood that the above-references features and controls are by way of example only, and the user interface can include other features and controls. It will be further understood that the pillow speaker controls, other remote controls, or controls including voice control or sip/puff can perform such functions or other functions in parallel with the systems and methods described herein.

It will be further understood that the mobile application program 1806 can be configured to display any number of other controls 2006 to control or otherwise interact with the facility application program 1818 operating on the facility application server 1810. It will be further understood that the mobile application program 1806 is configured to send and receive information and media content, such as text messages, video content, audio content, real-time communications, and other content.

The facility application program 1818 operating on the facility application server 1810 is configured to receive commands from the mobile application program 1806, analyze the information, and send instruction to the appropriate end-point device (in this case a flat screen television 1814 or other end point device) for the room and bed associated with a patient. The application 1824 running on the end-point device 1814 is configured to receive the information from the facility application program 1818 and perform the navigation desired, display the appropriate screen/feature, store/modify information stored for that patient (e.g. add personal notes for themselves), or perform the desired function.

Figure 21:
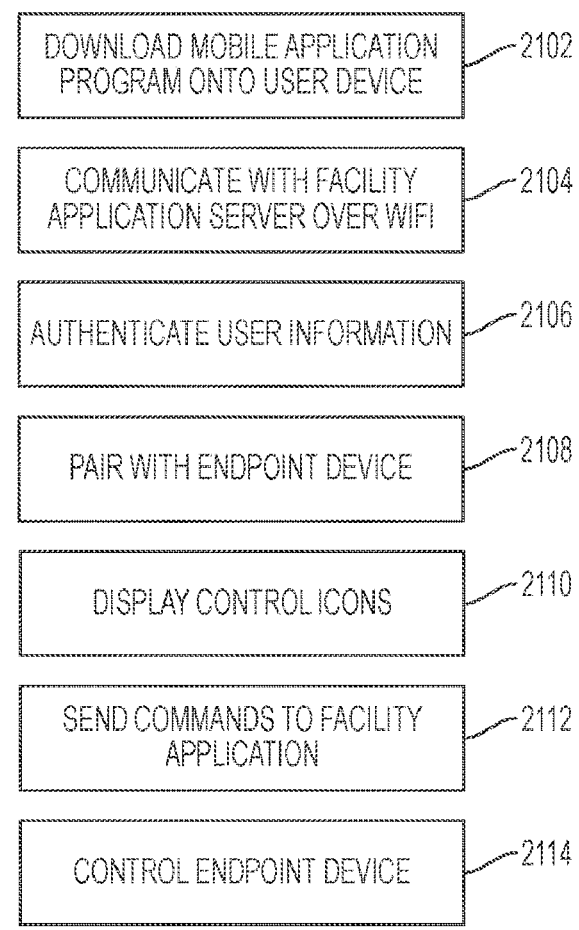
FIG. 21 illustrates a method for the control of media and communications systems, as shown and described herein.

Referring now to FIG. 21, a method 2100 for controlling a media and communications system is shown.

In step 2102 of method 2100, a user downloads onto a smartphone device 1802 a mobile application program 1806 from a mobile application server 1820 over the Internet and/or a wireless local area networking system 1808.

In step 2104 of method 2100, the mobile application program 1806 operating on the smartphone device 1802 communicates over a secured wireless local area networking system 1808 with the facility application server 1810. Such secured protocols may include WEP, WPA, WPA2 or other security that the organization may have implemented.

In step 2106 of method 2100, the user information is authenticated. For example, in a hospital setting, the information provided in this step could be the name of the patient along with visit/account number or medical record number.

In step 2108 of method 2100, the smartphone device 1802 is paired with the television 1814 or other end point device. For example, in a hospital setting, the information provided in this step is the room number. This step 2104 could be done via a QR scan on the TV in the patient room.

In step 2110 of method 2100, once authentication is complete, the appropriate control icons 2001 are displayed on the interface 2014, as determined by the mobile application program 1806 and facility application program 1818 on what controls will populate the display 2004. At this stage the user is able to start controlling the television 1814 or other end point device via the control icons 2001 or otherwise.

In step 2112 of method 2100, commands from the mobile application program 1806 are sent to the facility application program 1818 via APIs. These commands can be activated as a result various functions, including those described herein, such as through haptic contact engagement with the command icons 2001 through 2052, sip/puff, voice control, and/or other activations.

In step 2114 of method 2100, the command information received by the facility application program 1818 is processed by the facility application program 1818 and sent to the television 1814 or other end point device for appropriate action via APIs, resulting in user control over the television 1814 or other end point device.

In step 2116 of method 2100, if the information received from the mobile application program 1806 is not directly related to display on the television 1814 or other end point device, the facility application program 1818 might directly act on the data submitted to appropriately store/modify information stored for that patient (e.g. add personal notes for themselves) or trigger the activity desired by the specific command via other sets of APIs or interfaces (e.g. change room temperature).

It will be understood that not all of the steps in the methods described herein are required, or must be performed in the order as described herein.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A patient-related information delivery system for delivering patient-related information to a patient located in a hospital room, the patient-related information delivery system comprising:
   one or more virtual machine servers, wherein the one or more virtual machine servers are configured to be communicatively coupled to an electronic medical records database and one or more in-room devices, wherein the one or more in-room devices are configured to be utilized by the patient located in the hospital room; and
   one or more processors coupled to the one or more virtual machine servers, wherein the one or more processors are configured to:
      cause the one or more virtual machine servers to receive patient data from the electronic medical records database that relate to one or more patients;
      cause the one or more virtual machine servers to parse the patient data into a format usable by the one or more virtual machine servers, thereby creating parsed patient data;
      cause the one or more virtual machine servers to store the parsed patient data;
      cause the one or more virtual machine servers to enable the one or more in-room devices in the hospital room to receive and display the patient-related information;
      cause the one or more virtual machine servers to match the patient located in the hospital room to one of the one or more in-room devices; and
      cause the one or more virtual machine servers to send a command to the one of the one or more in-room devices to display the patient-related information.

2. The patient-related information delivery system of claim 1, wherein the patient data includes one or more of: patient admissions, discharge, transfer (ADT) data, patient medication data, nursing assessment data, orders and results data, diet orders data, and patient education data.

3. The patient-related information delivery system of claim 1, wherein the one or more in-room devices includes one or more of: a standard television, a smart television, a bedside terminal, a smart tablet, a smart phone, and a digital white board terminal.

4. The patient-related information delivery system of claim 1, wherein the displayed patient-related information includes one or more of: a patient name, a room information, and menu items relating to entertainment, meals, stay, care, and personalized information.

5. The patient-related information delivery system of claim 1, wherein the displayed patient-related information includes information from one or more of: a medication data module, a nursing assessment data module, an orders and results data module, a diet orders data module, a patient education module, a patients request and feedback module, a patient HVAC control module, a patient bedside monitoring module, and a patient entertainment module.

6. The patient-related information delivery system of claim 1, wherein the one or more processors are further configured to receive from the patient through a user interface on the one of the one or more in-room devices one or more of: a request, feedback data, meal orders data, and HVAC control data.

7. The patient-related information delivery system of claim 1, wherein the one or more processors are further configured to update patient-related information stored in the electronic medical records database.

8. A patient-related information delivery method for delivering patient-related information to a patient located in a hospital room, the patient-related information delivery method comprising:
   receiving, by one or more virtual machine servers, patient data from an electronic medical records database that relate to one or more patients;
   parsing, by the one or more virtual machine servers, the patient data into a format usable by the one or more virtual machine servers, thereby creating parsed patient data;
   storing, by the one or more virtual machine servers, the parsed patient data;
   enabling, by the one or more virtual machine servers, one or more in-room devices in the hospital room to receive and display the patient-related information;
   matching, by the one or more virtual machine servers, the patient located in the hospital room to one of the one or more in-room devices; and
   sending, by the one or more virtual machine servers, a command to the one of the one or more in-room devices to display the patient-related information.

9. The patient-related information delivery method of claim 8, wherein the patient data includes one or more of: patient admissions, discharge, transfer (ADT) data, patient medication data, nursing assessment data, orders and results data, diet orders data, and patient education data.

10. The patient-related information delivery method of claim 8, wherein the one or more in-room devices includes one or more of: a standard television, a smart television, a bedside terminal, a smart tablet, a smart phone, and a digital white board terminal.

11. The patient-related information delivery method of claim 8, wherein the displayed patient-related information includes one or more of: a patient name, a room information, and menu items relating to entertainment, meals, stay, care, and personalized information.

12. The patient-related information delivery method of claim 8, wherein the patient-related information includes information from one or more of: a medication data module, a nursing assessment data module, an orders and results data module, a diet orders data module, a patient education module, a patients request and feedback module, a patient HVAC control module, a patient bedside monitoring module, and a patient entertainment module.

13. The patient-related information delivery method of claim 8, wherein receiving patient data from the electronic medical records database that relate to one or more patients comprises receiving the patient data from multiple servers comprising the electronic medical records database.

14. The patient-related information delivery method of claim 8, further comprising receiving from the patient through a user interface on the one of the one or more in-room devices one or more of: a request, feedback data, meal orders data, and HVAC control data.

* * * * *